US012003863B2

(12) United States Patent
Yanagihara et al.

(10) Patent No.: US 12,003,863 B2
(45) Date of Patent: Jun. 4, 2024

(54) VIDEO PROCESSOR, ENDOSCOPE SYSTEM, AND IMAGE PROCESSING METHOD

(71) Applicant: OLYMPUS CORPORATION, Tokyo (JP)

(72) Inventors: Erika Yanagihara, Koganei (JP); Shinsuke Tani, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 359 days.

(21) Appl. No.: 17/379,194

(22) Filed: Jul. 19, 2021

(65) Prior Publication Data
US 2022/0060613 A1    Feb. 24, 2022

Related U.S. Application Data

(63) Continuation of application No. PCT/JP2019/001900, filed on Jan. 22, 2019.

(51) Int. Cl.
*H04N 23/74* (2023.01)
*A61B 1/00* (2006.01)
(Continued)

(52) U.S. Cl.
CPC ......... *H04N 23/74* (2023.01); *A61B 1/00016* (2013.01); *A61B 1/00032* (2013.01);
(Continued)

(58) Field of Classification Search
CPC ........ H04N 23/74; H04N 5/772; H04N 23/56; H04N 23/555; H04N 5/77; H04N 9/8042; H04N 23/65; A61B 1/00016; A61B 1/00032; A61B 1/00036; A61B 1/00066; A61B 1/06; A61B 1/128
See application file for complete search history.

(56) References Cited

U.S. PATENT DOCUMENTS

2009/0079819 A1*   3/2009   Abe ................... A61B 1/00016
                                                    348/E7.085

FOREIGN PATENT DOCUMENTS

JP    H01-204641 A    8/1989
JP    2638880 B2      8/1997
(Continued)

OTHER PUBLICATIONS

International Search Report dated Apr. 16, 2019 issued in PCT/JP2019/001900.

*Primary Examiner* — Michael E Teitelbaum
(74) *Attorney, Agent, or Firm* — Scully, Scott, Murphy & Presser, P.C.

(57) ABSTRACT

An endoscope system includes an endoscope, a video processor, a power source unit, and a parameter control device. The endoscope includes an image pickup unit and an illumination unit. The power source unit supplies electric power to the image pickup unit and the illumination unit. The video processor includes an image processing unit configured to generate an endoscope image. The parameter control device includes a data collection unit, a determination unit, and a parameter determination unit. When the data collection unit acquires one or more pieces of start information during execution of electric power consumption reducing processing, the determination unit determines to stop the electric power consumption reducing processing and execute high image quality achieving processing.

20 Claims, 9 Drawing Sheets

(51) Int. Cl.
  *A61B 1/06*    (2006.01)
  *A61B 1/12*    (2006.01)
  *H04N 5/77*    (2006.01)
  *H04N 23/50*   (2023.01)
  *H04N 23/56*   (2023.01)

(52) U.S. Cl.
  CPC ...... *A61B 1/00036* (2013.01); *A61B 1/00066* (2013.01); *A61B 1/06* (2013.01); *A61B 1/128* (2013.01); *H04N 5/772* (2013.01); *H04N 23/56* (2023.01); *H04N 23/555* (2023.01)

(56)          References Cited

FOREIGN PATENT DOCUMENTS

| | | |
|---|---|---|
| JP | 2007-29452 A | 2/2007 |
| JP | 2010-184054 A | 8/2010 |
| JP | 4800695 B2 | 10/2011 |
| JP | 2012-217486 A | 11/2012 |
| JP | 2018-148973 A | 9/2018 |
| WO | 2010-055938 A1 | 5/2010 |
| WO | 2016-052175 A1 | 4/2016 |
| WO | 2017/029839 A1 | 2/2017 |
| WO | 2018/203383 A1 | 11/2018 |
| WO | 2018/207537 A1 | 11/2018 |
| WO | 2020/152788 A1 | 7/2020 |
| WO | 2020/157909 A1 | 8/2020 |

\* cited by examiner

VIDEO PROCESSOR, ENDOSCOPE SYSTEM, AND IMAGE PROCESSING METHOD

CROSS REFERENCE TO RELATED APPLICATION

This application is a continuation application of PCT/JP2019/001900 filed on Jan. 22, 2019, the entire contents of which are incorporated herein by this reference.

BACKGROUND OF THE INVENTION

1. Field of the Invention

The present invention relates to a video processor, an endoscope system, and an image processing method that are capable of executing electric power consumption reducing processing and high image quality achieving processing.

2. Description of the Related Art

Recently, an endoscope device has been widely used in medical and industrial fields. In particular, an endoscope used in the medical field has been widely used for observation of an organ in a body cavity, medical treatment using a treatment instrument, a surgical operation under endoscope observation, and the like.

Recently, practical use of a battery-driven wireless endoscope on which a rechargeable battery is mounted has been started along with progress of semiconductor technologies and electric power consumption reduction due to use of an LED as an illumination light source. The wireless endoscope includes a wireless communication unit configured to perform wireless communication with a video processor, and compresses image data obtained through image pickup by an image pickup device and wirelessly transmits the compressed image data.

The wireless endoscope desirably can execute, as necessary, electric power consumption reducing processing that reduces an electric power consumption of the endoscope to prevent function decrease such as battery degradation by reducing internal temperature rise and to increase an operational time by reducing a consumption amount of the battery. In addition, to prevent wireless communication blackout, the wireless endoscope can desirably execute processing that changes a compression ratio of image data by, for example, increasing the compression ratio in a situation in which wireless environment is degraded, and decreasing the compression ratio to obtain an endoscope image of high image quality in an important scene.

WO 2017/029839 discloses a wireless endoscope configured to perform power saving operation that increases an image compression ratio and decreases an illumination light amount at battery replacement. Japanese Patent No. 4800695 discloses an endoscope device configured to reduce electric power consumption by controlling operation of each component of a body part of an endoscope device in accordance with internal temperature of the body part and an actual examination situation. WO 2016/052175 discloses a portable endoscope system configured to calculate a compression ratio of an endoscope image based on a result of determination of a procedure scene type.

SUMMARY OF THE INVENTION

A video processor according to an aspect of the present invention is a video processor including a processor. The processor is configured to: generate an endoscope image by performing predetermined image processing on image data obtained by a wireless endoscope that is battery-driven; acquire, as one or more pieces of start information after insertion of the wireless endoscope, at least one of information for starting video recording of the endoscope image or information for starting automatic diagnosis support processing using the endoscope image; and process the endoscope image. The processor performs, based on the one or more pieces of start information, determination of whether to execute or stop electric power consumption reducing processing that reduces electric power supplied from a power source, and determination of whether to execute or stop high image quality achieving processing that achieves high image quality of the endoscope image. When the processor acquires the one or more pieces of start information during execution of the electric power consumption reducing processing, the processor stops the electric power consumption reducing processing and executes the high image quality achieving processing.

An endoscope system according to an aspect of the present invention includes an endoscope, a video processor, and a power source. The endoscope includes an image pickup device configured to generate image data through image pickup of an object, and an illumination element configured to illuminate the object. The power source supplies electric power to the image pickup device and the illumination element. The video processor includes a processor. The processor is configured to: generate an endoscope image by performing predetermined image processing on the image data; acquire, as one or more pieces of start information, at least one of information for starting video recording of the endoscope image or information for starting automatic diagnosis support processing using the endoscope image; perform determination of whether to execute or stop electric power consumption reducing processing that reduces the electric power supplied from the power source and determination of whether to execute or stop high image quality achieving processing that achieves high image quality of the endoscope image; and determine one or more parameters used for processing that the processor determines to execute. When the processor acquires the one or more pieces of start information during execution of the electric power consumption reducing processing, the processor determines to stop the electric power consumption reducing processing and execute the high image quality achieving processing.

An image processing method according to an aspect of the present invention is an image processing method of generating an endoscope image from image data acquired by an image pickup device of a wireless endoscope. The image processing method includes: acquiring, as one or more pieces of start information after insertion of the wireless endoscope, at least one of information for starting video recording of the endoscope image or information for starting automatic diagnosis support processing using the endoscope image; performing, based on the one or more pieces of start information, determination of whether to execute or stop electric power consumption reducing processing that reduces electric power supplied from a power source and determination of whether to execute or stop high image quality achieving processing that achieves high image quality of the endo scope image; and stopping the electric power consumption reducing processing and executing the high image quality achieving processing when the one or more pieces of start information are acquired during execution of the electric power consumption reducing processing.

DETAILED DESCRIPTION OF THE PREFERRED EMBODIMENTS

Embodiments of the present invention will be described below with reference to the accompanying drawings.

First Embodiment (Configuration of Endoscope System)

Figure 1:
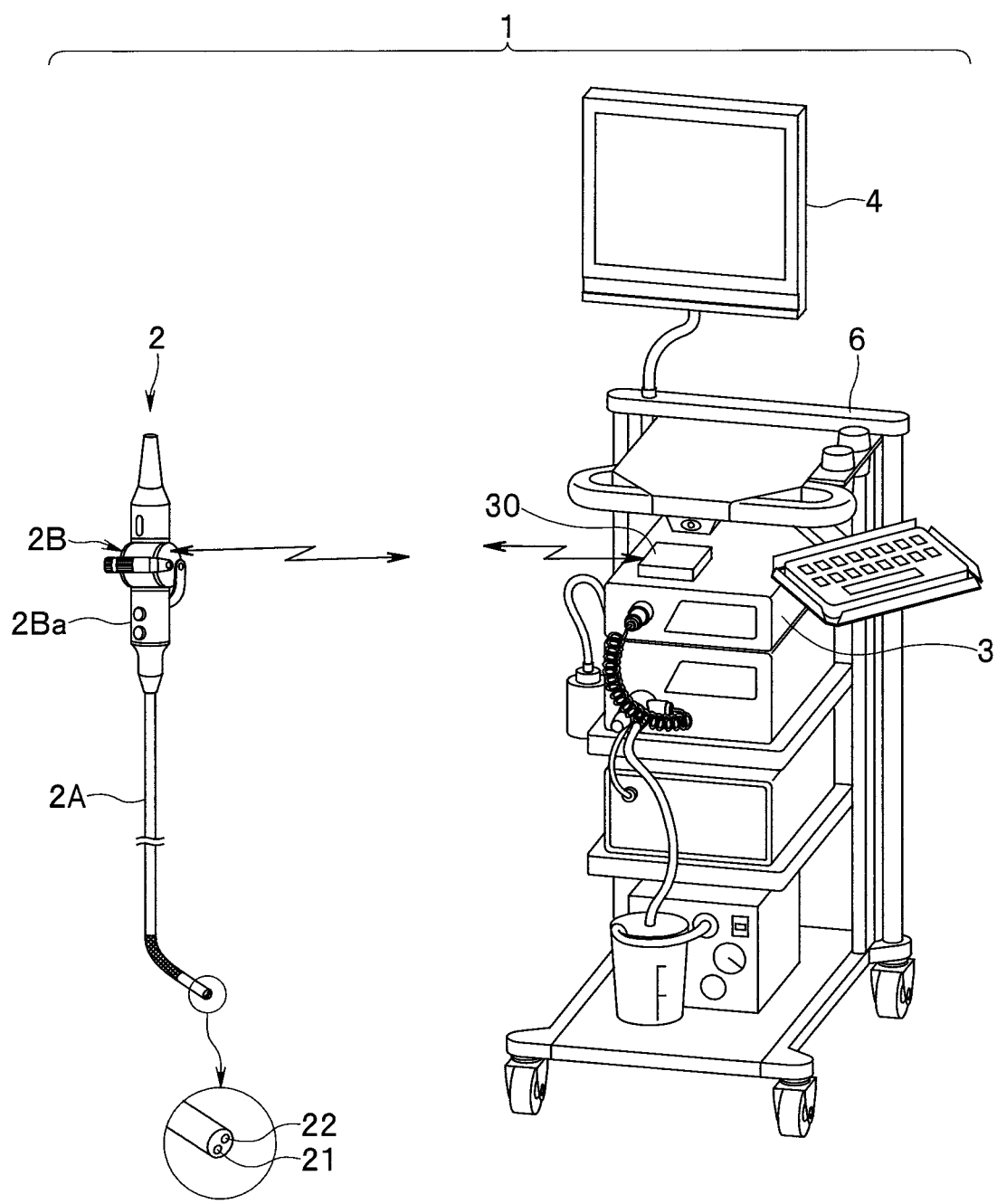
FIG. 1 is an explanatory diagram illustrating an entire configuration of an endoscope system according to a first embodiment of the present invention.

First, a schematic configuration of an endoscope system according to a first embodiment of the present invention will be described below. FIG. 1 is an explanatory diagram illustrating an entire configuration of an endoscope system 1 according to the present embodiment. The endoscope system 1 according to the present embodiment is a wireless endoscope system including a wireless endoscope 2 that is a battery-driven portable endoscope. Hereinafter, the wireless endoscope 2 is simply referred to as the endoscope 2.

The endoscope system 1 further includes a video processor 3 physically separated from the endoscope 2, and a display unit 4 connected to the video processor 3. The video processor 3 is wirelessly connected to the endoscope 2 and generates an endoscope image by performing predetermined image processing to be described later. The display unit 4 is configured of a monitor device or the like and displays the endoscope image and the like.

As illustrated in FIG. 1, the video processor 3, the display unit 4, and various medical instruments are placed on a cart 6 in an operation room. Examples of medical instruments placed on the cart 6 include devices such as an electrocautery scalpel device, a pneumoperitoneum apparatus, and a video recorder, and a gas cylinder filled with carbon dioxide.

Note that a configuration of the video processor 3 and the display unit 4 is not limited to an example illustrated in FIG. 1. For example, the endoscope system 1 may include a video processor integrated with a display unit in place of the video processor 3 and the display unit 4.

The endoscope 2 includes an elongated insertion portion 2A that is inserted into a body cavity, and an operation portion 2B including a grasping portion 2Ba that is grasped by a user. The operation portion 2B is provided at a proximal end portion of the insertion portion 2A.

The endoscope 2 further includes an image pickup unit 21 configured to generate image data through image pickup of an object, and an illumination unit 22 configured to illuminate the object. The object is a site such as an affected part in a subject. The image pickup unit 21 includes a non-illustrated image pickup device such as a CCD or a CMOS provided at a distal end portion of the insertion portion 2A.

The illumination unit 22 includes an illumination light source including a non-illustrated light-emitting element such as a light-emitting diode, and a non-illustrated lens provided at a distal end of the insertion portion 2A. Illumination light generated by the illumination light source is applied to the object through the lens. Return light of the illumination light from the object is imaged on an image pickup surface of the image pickup device of the image pickup unit 21. Note that the illumination light source may be provided in the operation portion 2B. In this case, the illumination light generated by the illumination light source is guided to the distal end of the insertion portion 2A through a non-illustrated light guide.

Figure 2:
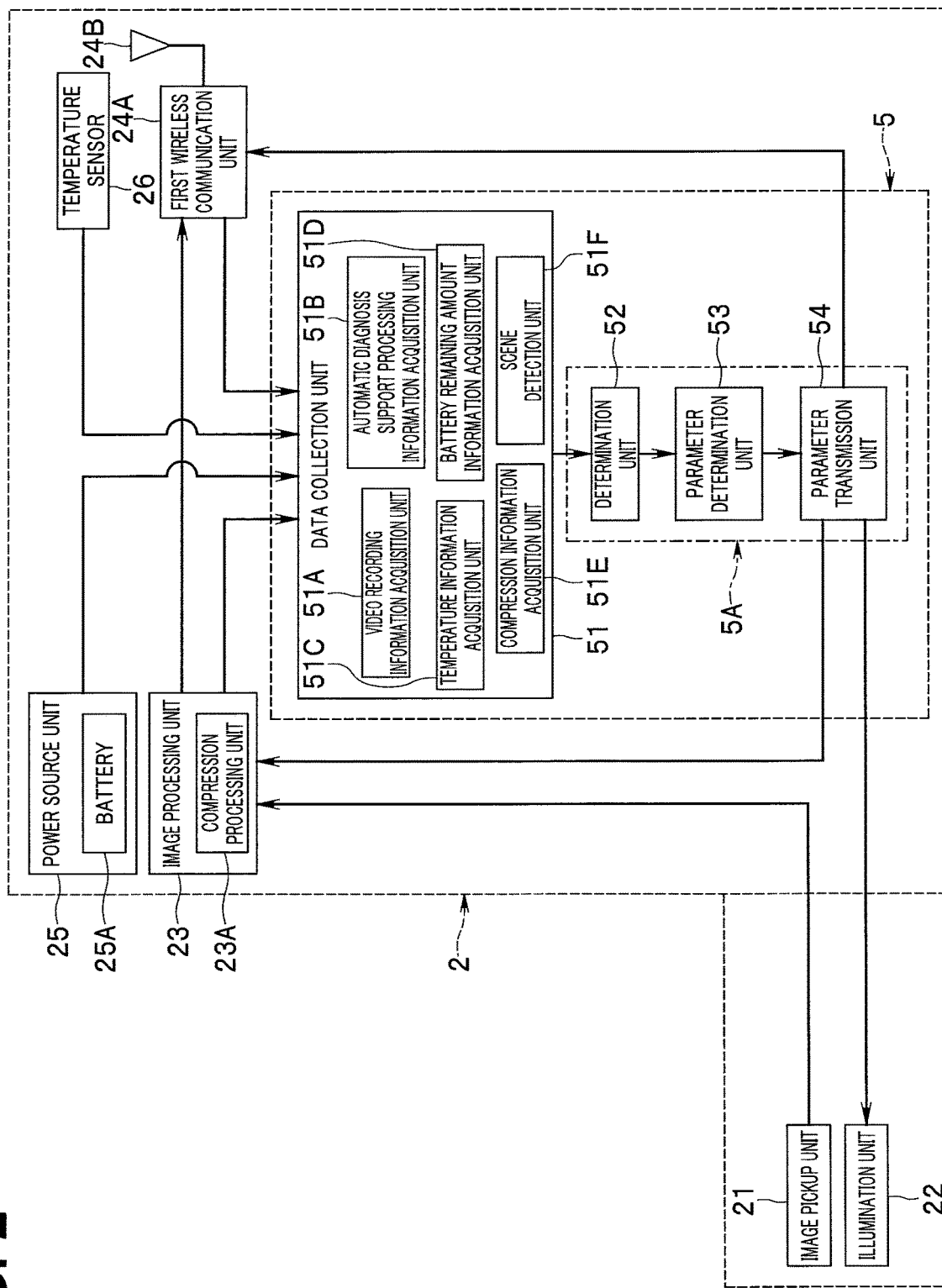
FIG. 2 is a functional block diagram illustrating configurations of an endoscope and a parameter control device of the endoscope system according to the first embodiment of the present invention.

The endoscope system 1 further includes a power source unit 25 and a parameter control device 5 according to the present embodiment. Note that the power source unit 25 and the parameter control device 5 are illustrated in FIG. 2 to be described later. The parameter control device 5 is a device that causes the endoscope 2 and the video processor 3 to execute predetermined processing by controlling a plurality of parameters used by the endoscope 2 and the video processor 3.

(Configurations of Endoscope and Parameter Control Device)

Subsequently, configurations of the endoscope 2 and the parameter control device 5 will be described below in detail with reference to FIG. 2. FIG. 2 is a functional block diagram illustrating the configurations of the endoscope 2 and the parameter control device 5. In the present embodiment, the entire parameter control device 5 is provided in the endoscope 2.

As illustrated in FIG. 2, the endoscope 2 includes an endoscope image processing unit (hereinafter simply referred to as an image processing unit) 23, a first wireless communication unit 24A, an antenna 24B, and a temperature sensor 26 in addition to the grasping portion 2Ba, the image pickup unit 21, and the illumination unit 22. The image pickup unit 21 generates image data based on an object optical image through photoelectric conversion and outputs the image data to the image processing unit 23.

The image processing unit 23 includes a compression processing unit 23A. The compression processing unit 23A performs compression processing that generates compressed data by compressing the image data generated by the image pickup unit 21. In the compression processing, a compression parameter that defines a data amount of the compressed data is used. The compression parameter has a compression ratio and a correspondence relation of the compressed data. The image processing unit 23 outputs the generated compressed data to the first wireless communication unit 24A and outputs the present compression parameter to the parameter control device 5. In addition, the image processing unit 23 outputs the image data for detecting an endoscope scene as information related to the endoscope scene to the parameter control device 5.

The first wireless communication unit 24A includes a non-illustrated wireless transmission circuit configured to generate a wirelessly transmitted signal, and a non-illustrated wireless reception circuit configured to demodulate a wirelessly received signal. The first wireless communication unit 24A wirelessly transmits and receives a predetermined signal to and from the video processor 3 through the antenna 24B. The predetermined signal includes compressed data, and parameters and start information to be described later.

Note that the first wireless communication unit 24A and a second wireless communication unit to be described later may be able to perform wireless communication by using a plurality of bands such as a 60-GHz band and a 5-GHz band. In this case, the 60-GHz band is used to, for example, transmit and receive compressed data. The 5-GHz band is used to, for example, transmit and receive a plurality of parameters.

The power source unit 25 is provided in the endoscope 2. The power source unit 25 includes a battery 25A provided in the endoscope 2 and supplies electric power of the battery 25A to each component of the endoscope 2 including the image pickup unit 21, the illumination unit 22, the image processing unit 23, and the first wireless communication unit 24A. The battery 25A is mountable on, for example, the operation portion 2B (refer to FIG. 1). In addition, the power source unit 25 includes a non-illustrated battery remaining amount detection circuit configured to detect a remaining amount of the battery 25A. The power source unit 25 outputs information of the detected remaining amount of the battery 25A to the parameter control device 5.

The temperature sensor 26 is able to measure temperature of the grasping portion 2Ba (refer to FIG. 1), and outputs a measurement result of the temperature of the grasping portion 2Ba to the parameter control device 5. Note that the endoscope 2 may include, in addition to the temperature sensor 26, one or more temperature sensors configured to measure temperature of each component of the endoscope 2 except for the grasping portion 2Ba and the temperature sensor 26.

As illustrated in FIG. 2, the parameter control device 5 includes a data collection unit 51, a determination unit 52, a parameter determination unit 53, and a parameter transmission unit 54. The determination unit 52, the parameter determination unit 53, and the parameter transmission unit 54 are included in a control unit 5A as a main part of the parameter control device 5. In other words, the determination unit 52 and the parameter determination unit 53 are provided in the endoscope 2. The data collection unit 51 acquires a plurality of pieces of information related to the endoscope system 1. A configuration of the data collection unit 51 will be described later.

Processing that reduces electric power supplied from the power source unit 25 is referred to as electric power consumption reducing processing. In the present embodiment, in particular, the electric power consumption reducing processing is processing that reduces electric power of the battery 25A supplied from the power source unit 25. Processing that achieves high image quality of the endoscope image generated by the video processor 3 is referred to as high image quality achieving processing. The determination unit 52 determines the plurality of pieces of information acquired by the data collection unit 51, thereby performing determination of whether to execute or stop the electric power consumption reducing processing and determination of whether to execute or stop the high image quality achieving processing. The parameter determination unit 53 determines one or more parameters used for processing that the determination unit 52 determines to execute.

The parameter transmission unit 54 transmits the one or more parameters determined by the parameter determination unit 53 to each component of the endoscope 2 and the video processor 3. In the endoscope 2, the illumination unit 22 and the compression processing unit 23A receive the parameters transmitted from the parameter transmission unit 54. In the video processor 3, a main control unit to be described later receives the parameters transmitted from the parameter transmission unit 54.

The endoscope 2 further includes a non-illustrated main control unit. The main control unit controls each component of the endoscope 2 including the parameter control device 5, and also controls the power source unit 25 to supply power to each component of the endoscope 2 including the parameter control device 5.

(Configuration of Video Processor)

Figure 3:
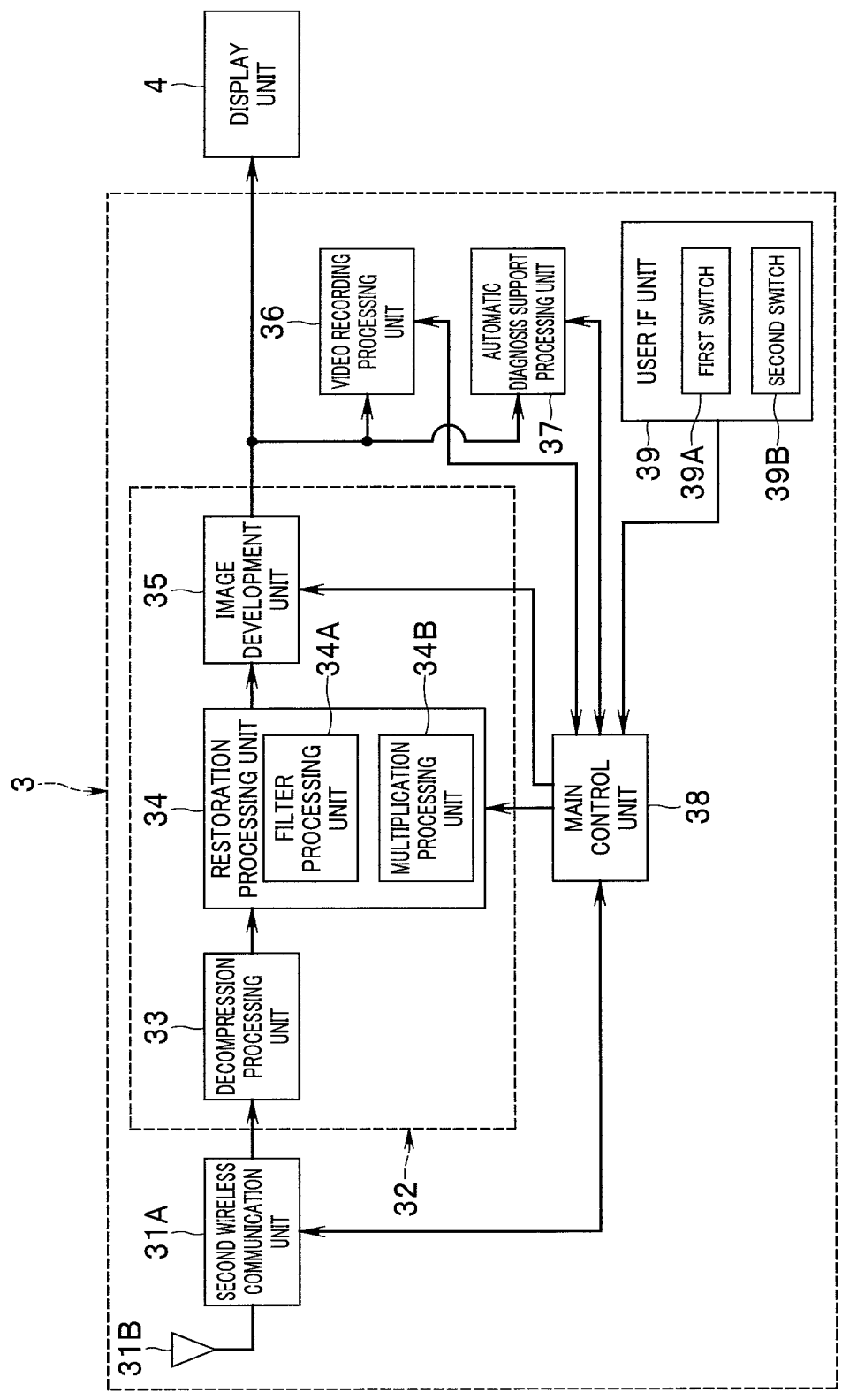
FIG. 3 is a functional block diagram illustrating configurations of a video processor and a display unit of the endoscope system according to the first embodiment of the present invention.

Subsequently, a configuration of the video processor 3 will be described below with reference to FIG. 3. FIG. 3 is a functional block diagram illustrating a configuration of the video processor 3 and the display unit 4. As illustrated in FIG. 3, the video processor 3 includes a second wireless communication unit 31A, an antenna 31B, a processor image processing unit (hereinafter simply referred to as an image processing unit) 32, a video recording processing unit 36, an automatic diagnosis support processing unit 37, a main control unit 38, and a user interface unit (hereinafter referred to as a user IF unit) 39.

The second wireless communication unit 31A and the antenna 31B may be built in a main body of the video processor 3 or may be built in a wireless receiver 30 separated from the main body of the video processor 3. FIG. 1 illustrates the wireless receiver 30. The wireless receiver 30 is connected to the main body of the video processor 3 through a non-illustrated connector.

The second wireless communication unit 31A includes a non-illustrated wireless transmission circuit configured to generate a wirelessly transmitted signal, and a non-illustrated wireless reception circuit configured to demodulate a wirelessly received signal. The second wireless communication unit 31A wirelessly transmits and receives a predetermined signal to and from the endoscope 2 through the antenna 31B. The predetermined signal includes the compressed data transmitted by the first wireless communication unit 24A, the one or more parameters transmitted by the parameter transmission unit 54, and the start information to be described later. The second wireless communication unit 31A outputs the compressed data to the image processing unit 32, and outputs the one or more parameters to the main control unit 38.

The image processing unit 32 generates image data by decompressing the compressed data and also generates an endoscope image by performing predetermined image processing on the image data generated by decompressing the compressed data. Hereinafter, the image data generated by decompressing the compressed data is referred to as decompressed image data. The decompressed image data is data corresponding to the image data generated by the image pickup unit 21. In the present embodiment, the image processing unit 32 includes a decompression processing unit 33 configured to generate the decompressed image data, a restoration processing unit 34, and an image development unit 35.

The restoration processing unit 34 performs at least one piece of image restoration processing on the decompressed image data to improve image quality of the endoscope image. In the present embodiment, in particular, the restoration processing unit 34 is able to perform, as the at least one piece of image restoration processing, brightness correction processing that corrects brightness of the decompressed image data. Specifically, the restoration processing unit 34 includes a filter processing unit 34A and a multiplication processing unit 34B that execute the brightness correction processing.

The filter processing unit 34A performs filter processing that corrects brightness of any one pixel of the decompressed image data by using a plurality of pixel values in a predetermined region including the one pixel and a plurality of pixels surrounding the one pixel, and a first brightness parameter. The filter processing may be, for example, processing that, for each channel of RGB, multiplies values of brightness of the plurality of surrounding pixels by coefficients (weights) and adds the multiplied values to a value of brightness of the one pixel. In this case, the first brightness parameter may be the coefficients (weights) by which the values of brightness of the plurality of pixels are multiplied.

The multiplication processing unit 34B performs multiplication processing that corrects brightness of any one pixel by using a pixel value of the one pixel and a second brightness parameter. The multiplication processing may be processing that multiplies a luminance value of the one pixel by the second brightness parameter as a multiplier. In this case, the second brightness parameter may be a constant or may be a value that changes in accordance with the luminance value as in gamma correction. In the latter case, the multiplication processing is performed by using a table indicating a relation between the luminance value and the second brightness parameter.

Note that, as an effect of the filter processing is stronger, the decompressed image data after correction is brighter but a resolution of the decompressed image data after correction is lower. In addition, as an effect of the multiplication processing is stronger, the decompressed image data after correction is brighter but noise of the decompressed image data after correction is larger. Thus, in order to obtain the endoscope image of high image quality and high resolution by performing the filter processing and the multiplication processing so that the endoscope image becomes brighter, it is needed to set the first brightness parameter to avoid excess decrease of the resolution of the decompressed image data after correction, and to set the second brightness parameter to avoid excess increase of the noise of the decompressed image data after correction.

The image development unit 35 performs image development processing that generates the endoscope image by converting the decompressed image data into a format displayable on the display unit 4. The image processing unit 32 outputs the generated endoscope image to the video recording processing unit 36, the automatic diagnosis support processing unit 37, and the display unit 4.

The user IF unit 39 is an interface configured to receive a user operation. Specifically, the user IF unit 39 includes, for example, a front panel and various switches of a control system, and outputs an operation signal based on the user operation to the main control unit 38. Examples of the user operation include activation of the endoscope system 1, power-off of the endoscope system 1, start and stop of video recording of the endoscope image, start and stop of automatic diagnosis support processing, specification of an observation mode of the endoscope 2, setting related to image display, and setting of an operation mode of the endoscope 2.

In the present embodiment, in particular, the user IF unit 39 includes a first switch 39A through which start and stop of the video recording of the endoscope image are instructed, and a second switch 39B through which start and stop of the automatic diagnosis support processing are instructed. An operation signal that instructs start or stop of the video recording of the endoscope image is generated as the user operates the first switch 39A. An operation signal that instructs start or stop of the automatic diagnosis support processing is generated as the user operates the second switch 39B.

The main control unit 38 controls each component of the video processor 3 and also controls a non-illustrated power source unit provided in the video processor 3 to supply power to each component of the video processor 3. The main control unit 38 receives a parameter transmitted from the parameter transmission unit 54 and outputs the received parameter to the restoration processing unit 34. The main control unit 38 outputs information based on an operation signal inputted through the user IF unit 39 to each component of the video processor 3, and also outputs the information to the non-illustrated main control unit and the parameter control device 5 of the endoscope 2 through wireless communication between the endoscope 2 and the video processor 3. Accordingly, the main control unit 38 can provide various instructions based on an operation signal to each component of the endoscope 2, the video processor 3, and the parameter control device 5.

In the present embodiment, in particular, the main control unit 38 generates, based on an operation signal that instructs start or stop of the video recording of the endoscope image, information for starting the video recording of the endoscope image and information for stopping the video recording of the endoscope image, and outputs these pieces of information to the video recording processing unit 36 and the parameter control device 5. In addition, the main control unit 38 generates, based on an operation signal that instructs start or stop of the automatic diagnosis support processing, information for starting the automatic diagnosis support processing and information for stopping the automatic diagnosis support processing, and outputs these pieces of information to the automatic diagnosis support processing unit 37 and the parameter control device 5.

The video recording processing unit 36 performs video recording processing that video-records the endoscope image generated by the image development unit 35. In the present embodiment, the video recording processing unit 36 starts the video recording processing when the information for starting the video recording of the endoscope image is inputted, and stops the video recording processing when the information for stopping the video recording of the endoscope image is inputted. Note that, after outputting the information for starting the video recording of the endoscope image to the video recording processing unit 36, the main control unit 38 controls the image development unit 35 to output the endoscope image to the video recording processing unit 36. The video recording processing unit 36 includes a non-illustrated storage unit configured to store the endoscope image video-recorded by the video recording processing. The video recording processing unit 36 may be able to output the endoscope image stored in the storage unit to the display unit 4 and a non-illustrated storage device configured of a non-transitory memory.

The endoscope image video-recorded by the video recording processing is used, for example, for production of a diagnosis report or for detailed diagnosis to be performed later. To improve accuracy of the detailed diagnosis, the endoscope image video-recorded by the video recording processing needs to be an image of high image quality.

The automatic diagnosis support processing unit 37 performs the automatic diagnosis support processing using the endoscope image. In the present embodiment, the automatic diagnosis support processing unit 37 starts the automatic diagnosis support processing when the information for starting the automatic diagnosis support processing is inputted, and stops the automatic diagnosis support processing when the information for stopping the automatic diagnosis support processing is inputted. Note that, after outputting the information for starting the automatic diagnosis support processing to the video recording processing unit 36, the main control unit 38 controls the image development unit 35 to output the endoscope image to the automatic diagnosis support processing unit 37. The automatic diagnosis support processing unit 37 may be able to output a result of the automatic diagnosis support processing to the display unit 4.

The automatic diagnosis support processing is, for example, processing that automatically detects existence of anomaly by analyzing the endoscope image generated by the image development unit 35 through image processing or the like. The analysis of the endoscope image is performed by, for example, image processing using artificial intelligence. To improve accuracy of automatic diagnosis, the endoscope image used in the automatic diagnosis support processing needs to be an image of high image quality.

(Hardware Configuration)

Figure 4:
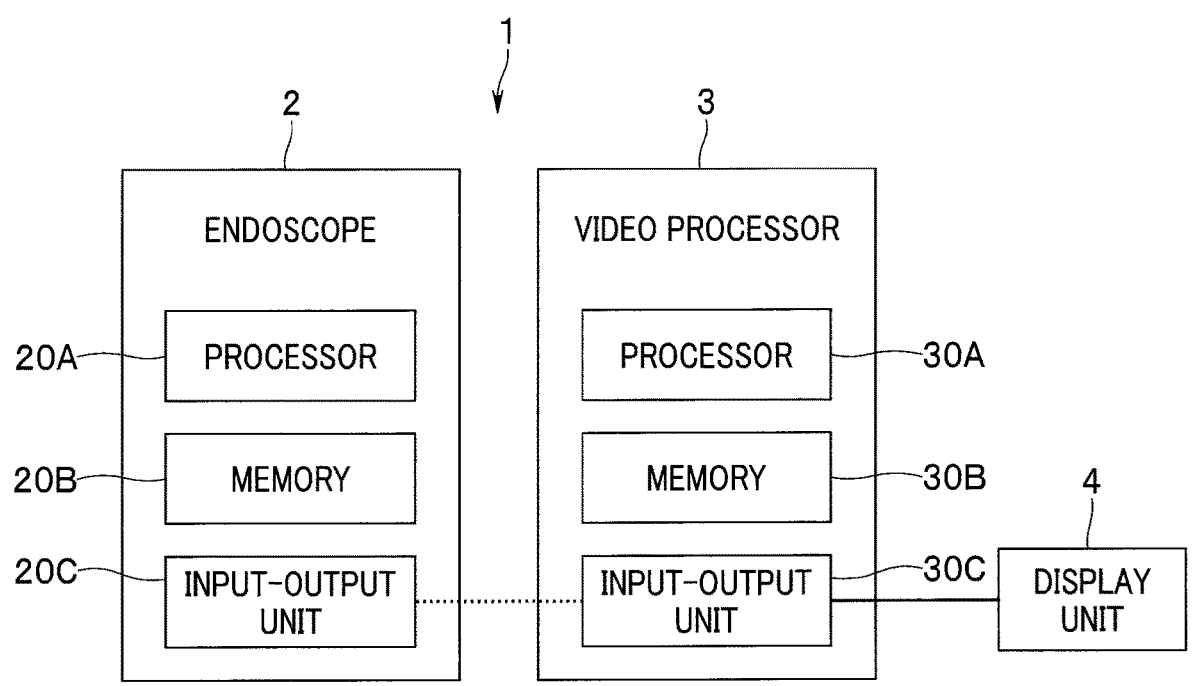
FIG. 4 is an explanatory diagram illustrating an example of a hardware configuration of the endoscope system according to the first embodiment of the present invention.

Subsequently, a hardware configuration of the endoscope system 1 will be described below with reference to FIG. 4. FIG. 4 is an explanatory diagram illustrating an example of the hardware configuration of the endoscope system 1. In the example illustrated in FIG. 4, the endoscope 2 includes a processor 20A, a memory 20B, and an input-output unit 20C. The video processor 3 includes a processor 30A, a memory 30B, and an input-output unit 30C.

The processor 20A is used to execute functions of the image processing unit 23, the first wireless communication unit 24A, the power source unit 25, the non-illustrated main control unit, and the like as components of the endoscope 2, and functions of the data collection unit 51, the determination unit 52, the parameter determination unit 53, and the parameter transmission unit 54 as components of the parameter control device 5. The processor 30A is used to execute functions of the second wireless communication unit 31A, the image processing unit 32, the video recording processing unit 36, the automatic diagnosis support processing unit 37, the main control unit 38, and the like as components of the video processor 3. The processors 20A and 30A are each configured of, for example, a field programmable gate array (FPGA). At least some of a plurality of components of the endoscope 2, the video processor 3, and the parameter control device 5 may be configured as circuit blocks in the FPGA.

The memories 20B and 30B are each configured of a rewritable storage element such as RAM. The input-output unit 20C is used to perform signal transmission and reception between the endoscope 2 and outside. The input-output unit 30C is used to perform signal transmission and reception between the video processor 3 and outside. In the present embodiment, in particular, wireless signal transmission and reception between the endoscope 2 and the video processor 3 are performed by using the input-output units 20C and 30C.

Note that the processors 20A and 30A may be each configured of a central processing unit (hereinafter referred to as a CPU). In this case, the functions of components of the endoscope 2 and the parameter control device 5 may be achieved as the CPU reads a program from the memory 20B or a non-illustrated storage device and executes the program. Similarly, the functions of components of the video processor 3 may be achieved as the CPU reads a program from the memory 30B or a non-illustrated storage device and executes the program.

The hardware configuration of the endoscope system 1 is not limited to the example illustrated in FIG. 4. For example, a plurality of components of the endoscope 2, the video processor 3, and the parameter control device 5 may be each configured as a separate electronic circuit.

(Operation of Parameter Control Device)

Subsequently, operation of the parameter control device 5 will be described below.

(Configuration and Operation of Data Collection Unit)

First, a configuration and operation of the data collection unit 51 will be described below with reference to FIG. 2. The data collection unit 51 acquires one or more pieces of start information as the plurality of pieces of information. In the present embodiment, the data collection unit 51 acquires, as the one or more pieces of start information, at least one of the information for starting the video recording of the endoscope image or the information for starting the automatic diagnosis support processing.

The data collection unit 51 further acquires one or more pieces of environment information as the plurality of pieces of information. In the present embodiment, the data collection unit 51 acquires, as the one or more pieces of environment information, at least one of information related to the temperature of the grasping portion 2Ba or information related to the remaining amount of the battery 25A.

The data collection unit 51 further acquires, as the plurality of pieces of information, the information for stopping the video recording of the endoscope image and the information for stopping the automatic diagnosis support processing.

In the present embodiment, the data collection unit 51 includes a video recording information acquisition unit 51A, an automatic diagnosis support processing information acquisition unit 51B, a temperature information acquisition unit 51C, and a battery remaining amount information acquisition unit 51D. In other words, the video recording information acquisition unit 51A, the automatic diagnosis support processing information acquisition unit 51B, the temperature information acquisition unit 51C, and the battery remaining amount information acquisition unit 51D are provided in the endoscope 2.

The video recording information acquisition unit 51A acquires the information for starting the video recording of the endoscope image and the information for stopping the video recording of the endoscope image. In the present embodiment, the video recording information acquisition unit 51A receives the information for starting the video recording of the endoscope image and the information for stopping the video recording of the endoscope image, which are outputted from the main control unit 38 (refer to FIG. 3) of the video processor 3.

The automatic diagnosis support processing information acquisition unit 51B acquires the information for starting the automatic diagnosis support processing and the information for stopping the automatic diagnosis support processing. In the present embodiment, the automatic diagnosis support processing information acquisition unit 51B receives the information for starting the automatic diagnosis support processing and the information for stopping the automatic diagnosis support processing, which are outputted from the main control unit 38 (refer to FIG. 3) of the video processor 3.

The temperature information acquisition unit 51C acquires the information related to the temperature of the grasping portion 2Ba. In the present embodiment, the temperature information acquisition unit 51C receives the measurement result of the temperature of the grasping portion 2Ba, which is outputted from the temperature sensor 26.

The battery remaining amount information acquisition unit 51D acquires the information related to the remaining amount of the battery 25A. In the present embodiment, the battery remaining amount information acquisition unit 51D receives the information related to the remaining amount of the battery 25A, which is outputted from the power source unit 25.

The data collection unit 51 further includes a compression information acquisition unit 51E and a scene detection unit 51F. The compression information acquisition unit 51E acquires information related to the compression processing. In the present embodiment, the compression information acquisition unit 51E receives the compression parameter outputted from the image processing unit 23.

The scene detection unit 51F acquires information related to an endoscope scene. In the present embodiment, image data for detecting an endoscope scene is outputted from the image processing unit 23 and inputted to the scene detection unit 51F. The scene detection unit 51F detects an endoscope scene by analyzing the image data. Examples of the endoscope scene include a detailed-check scene corresponding to a case of detailed-check observation of a blood vessel or the like, a screening scene corresponding to, for example, a case of search for an anomalous part while moving the insertion portion 2A, and an external scene corresponding to a case of external positioning of the insertion portion 2A.

(Operation of Determination Unit)

Subsequently, operation of the control unit 5A of the parameter control device 5, in other words, operation of the determination unit 52, the parameter determination unit 53, and the parameter transmission unit 54 will be described below with reference to FIGS. 2 and 3. First, the operation of the determination unit 52 will be described below. The determination unit 52 determines whether to execute or stop the high image quality achieving processing by confirming whether the information for starting or stopping the video recording of the endoscope image and the information for starting or stopping the automatic diagnosis support processing are acquired by the data collection unit 51. Specifically, the determination unit 52 determines to execute the high image quality achieving processing when at least one of acquisition of the information for starting the video recording of the endoscope image by the video recording information acquisition unit 51A or acquisition of the information for starting the automatic diagnosis support processing by the automatic diagnosis support processing information acquisition unit 51B is confirmed.

The determination unit 52 determines to stop the high image quality achieving processing when acquisition of the information for stopping the video recording of the endoscope image by the video recording information acquisition unit 51A is confirmed during execution of the video recording processing. The determination unit 52 determines to stop the high image quality achieving processing when acquisition of the information for stopping the automatic diagnosis support processing by the automatic diagnosis support processing information acquisition unit 51B is confirmed during execution of the automatic diagnosis support processing.

Note that the determination unit 52 may receive information of whether the video recording processing is in execution and information of whether the automatic diagnosis support processing is in execution. These pieces of information may be outputted from, for example, the main control unit 38 of the video processor 3. Alternatively, the determination unit 52 may determine whether the video recording processing is in execution based on the information for starting or stopping the video recording of the endoscope image, which is acquired by the video recording information acquisition unit 51A. Similarly, the determination unit 52 may determine whether the automatic diagnosis support processing is in execution based on the information for starting or stopping the automatic diagnosis support processing, which is acquired by the automatic diagnosis support processing information acquisition unit 51B.

The high image quality achieving processing is processing that achieves higher image quality of the endoscope image than when the high image quality achieving processing is not executed. In the present embodiment, the high image quality achieving processing includes illumination light amount change processing that changes an illumination light amount of the illumination unit 22, compression amount change processing that changes the data amount of the compressed data, and the brightness correction processing performed by the restoration processing unit 34. The illumination light amount change processing is processing in which an illumination parameter that defines the illumination light amount of the illumination unit 22 is used. The compression amount change processing is processing in which a compression parameter that defines the data amount of the compressed data is used. The brightness correction processing is processing in which a brightness parameter that defines a relation between brightness of the decompressed image data before correction and brightness of the decompressed image data after correction is used.

The determination unit 52 determines whether to execute the electric power consumption reducing processing by determining the information related to the temperature of the grasping portion 2Ba, which is acquired by the temperature information acquisition unit 51C, and the information related to the remaining amount of the battery 25A, which is acquired by the battery remaining amount information acquisition unit 51D. Specifically, the determination unit 52 determines whether the temperature of the grasping portion 2Ba is equal to or higher than a predetermined temperature threshold value, and determines whether the remaining amount of the battery 25A is smaller than a predetermined battery threshold value. The determination unit 52 determines to execute the electric power consumption reducing processing when at least one of a condition that the temperature of the grasping portion 2Ba is equal to or higher than the predetermined temperature threshold value or a condition that the remaining amount of the battery 25A is smaller than the predetermined battery threshold value is satisfied.

The electric power consumption reducing processing is processing that operates the endoscope 2 so that consumption of electric power of the battery 25A is smaller than when the electric power consumption reducing processing is not executed. The electric power consumption reducing processing includes at least the illumination light amount change processing and the brightness correction processing among the illumination light amount change processing, the compression amount change processing, and the brightness correction processing.

The determination unit 52 determines to stop the electric power consumption reducing processing and execute the high image quality achieving processing when at least one of acquisition of the information for starting the video recording of the endoscope image by the video recording information acquisition unit 51A or acquisition of the information for starting the automatic diagnosis support processing by the automatic diagnosis support processing information acquisition unit 51B is confirmed during execution of the electric power consumption reducing processing.

Note that the determination unit 52 may receive information of whether the electric power consumption reducing processing is in execution. This information may be outputted from, for example, the main control unit of the endoscope 2. Alternatively, the determination unit 52 may determine whether the electric power consumption reducing processing is in execution based on determination of whether to execute the electric power consumption reducing processing, which is performed by the determination unit 52.

(Operation of Parameter Determination Unit)

Subsequently, the operation of the parameter determination unit 53 will be described below. The operation of the parameter determination unit 53, which is related to the high image quality achieving processing is as follows. When the determination unit 52 determines to execute the high image quality achieving processing, the parameter determination unit 53 determines the illumination parameter so that the illumination light amount is larger than when the high image quality achieving processing is not executed, determines the compression parameter so that the compression ratio is lower, in other words, the data amount of the compressed data is larger than when the high image quality achieving processing is not executed, and determines the brightness parameter so that an effect of the brightness correction processing that brightens the endoscope image is weaker than when the high image quality achieving processing is not executed.

In the present embodiment, the parameter determination unit 53 determines, as the brightness parameter, the first brightness parameter used in the filter processing and the second brightness parameter used in the multiplication processing. When the determination unit 52 determines to execute the high image quality achieving processing, the parameter determination unit 53 determines the first brightness parameter so that the effect of the filter processing is weaker than when the high image quality achieving processing is not executed, and determines the second brightness parameter so that the effect of the multiplication processing is weaker than when the high image quality achieving processing is not executed.

The operation of the parameter determination unit 53, which is related to the electric power consumption reducing processing is as follows. When the determination unit 52 determines to execute the illumination light amount change processing as the electric power consumption reducing processing, the parameter determination unit 53 determines the illumination parameter so that the illumination light amount is smaller than when the electric power consumption reducing processing is not executed. When the determination unit 52 determines to execute the compression amount change processing as the electric power consumption reducing processing, the parameter determination unit 53 determines the compression parameter so that the compression ratio is higher, in other words, the data amount of the compressed data is smaller than when the electric power consumption reducing processing is not executed. When the determination unit 52 determines to execute the brightness correction processing as the electric power consumption reducing processing, the parameter determination unit 53 determines the brightness parameter so that the effect of the brightness correction processing that brightens the endoscope image is stronger than when the electric power consumption reducing processing is not executed.

As described above, in the present embodiment, the parameter determination unit 53 determines, as the brightness parameter, the first brightness parameter used in the filter processing and the second brightness parameter used in the multiplication processing. When the determination unit 52 determines to execute the electric power consumption reducing processing, the first brightness parameter is determined so that the effect of the filter processing is stronger than when the electric power consumption reducing processing is not executed, and the second brightness parameter is determined so that the effect of the multiplication processing is stronger than when the electric power consumption reducing processing is not executed.

Note that the compression parameter can change in accordance with contents of image data. In the present embodiment, the parameter determination unit 53 may receive the compression parameter acquired by the compression information acquisition unit 51E. In this case, the parameter determination unit 53 may determine the compression parameter used in next compression processing based on a result of the determination by the determination unit 52 and the compression parameter used in the compression processing right before.

The parameters other than the compression parameter may be fixed values or may be values that change in accordance with contents of image data Each parameter may be stored in a non-illustrated storage device provided in the endoscope 2 or the parameter control device 5.

(Operation of Parameter Transmission Unit)

Subsequently, the operation of the parameter transmission unit 54 will be described below. The parameter transmission unit 54 transmits the illumination parameter to the illumination unit 22, transmits the compression parameter to the compression processing unit 23A, and transmits the first and second brightness parameters to the main control unit 38 of the video processor 3. The illumination unit 22 changes the illumination light amount of the illumination unit 22 based on the received illumination parameter. The compression processing unit 23A performs the compression processing by using the received compression parameter.

The main control unit 38 outputs the received first brightness parameter to the filter processing unit 34A of the restoration processing unit 34, and outputs the received second brightness parameter to the multiplication processing unit 34B of the restoration processing unit 34. The filter processing unit 34A performs the filter processing by using the first brightness parameter. The multiplication processing unit 34B performs the multiplication processing by using the second brightness parameter.

(Standard Processing)

Processing that the parameter control device 5 causes the endoscope 2 and the video processor 3 to execute when the electric power consumption reducing processing and the high image quality achieving processing are not executed is referred to as standard processing. The determination unit 52 determines to execute the standard processing w % ben the determination unit 52 does not determine to execute the electric power consumption reducing processing and does not determine to execute the high image quality achieving processing. In this case, the determination unit 52 may determine contents of the standard processing by determining the information related to an endoscope scene, which is acquired by the scene detection unit 51F. The parameter determination unit 53 determines the illumination parameter, the compression parameter, the first brightness parameter, and the second brightness parameter used for the standard processing of contents determined by the determination unit 52.

(A Series of Operations Related to Parameter Control Device)

Figure 5:
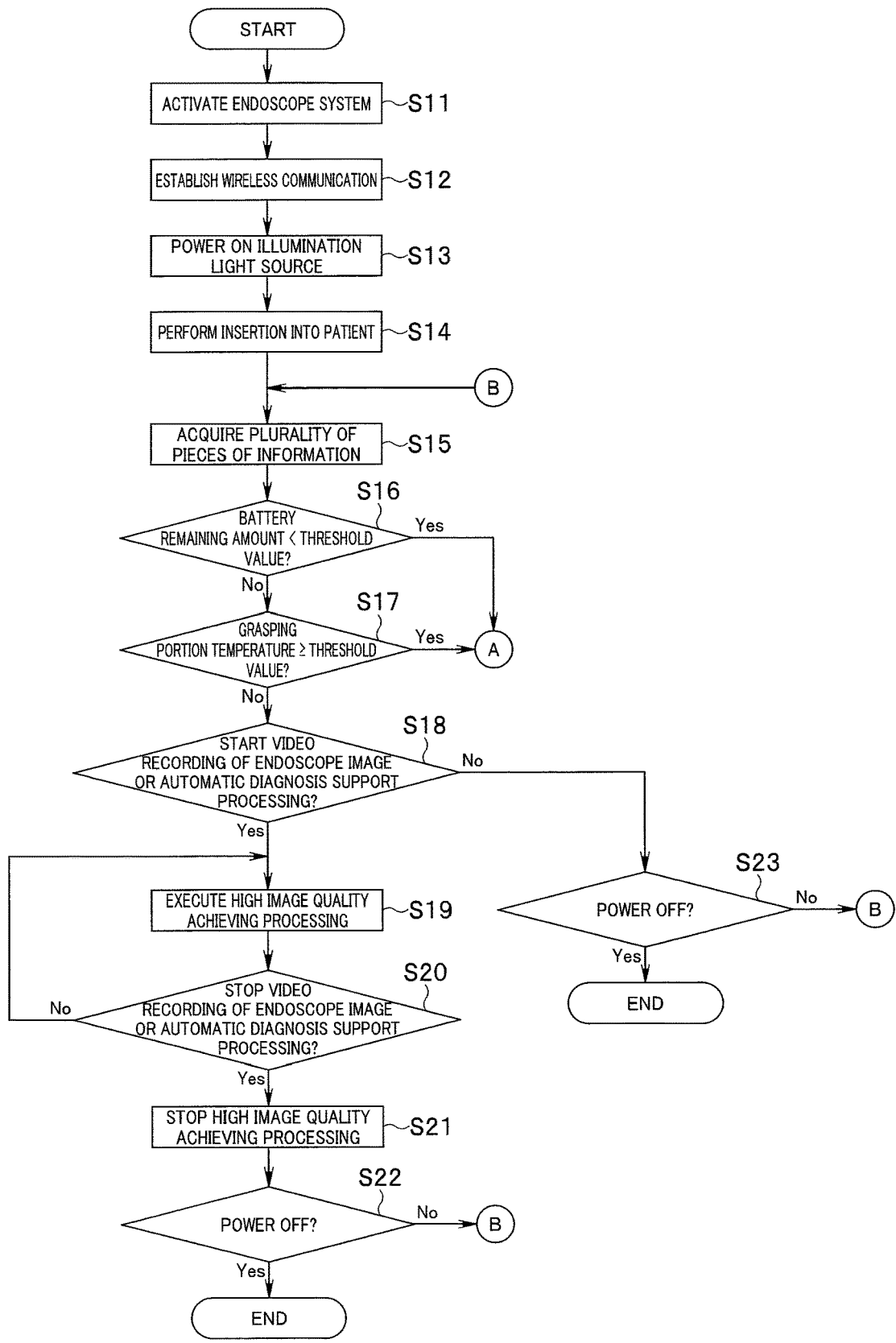
FIG. 5 is a flowchart illustrating part of operation of the endoscope system according to the first embodiment of the present invention.
Figure 6:
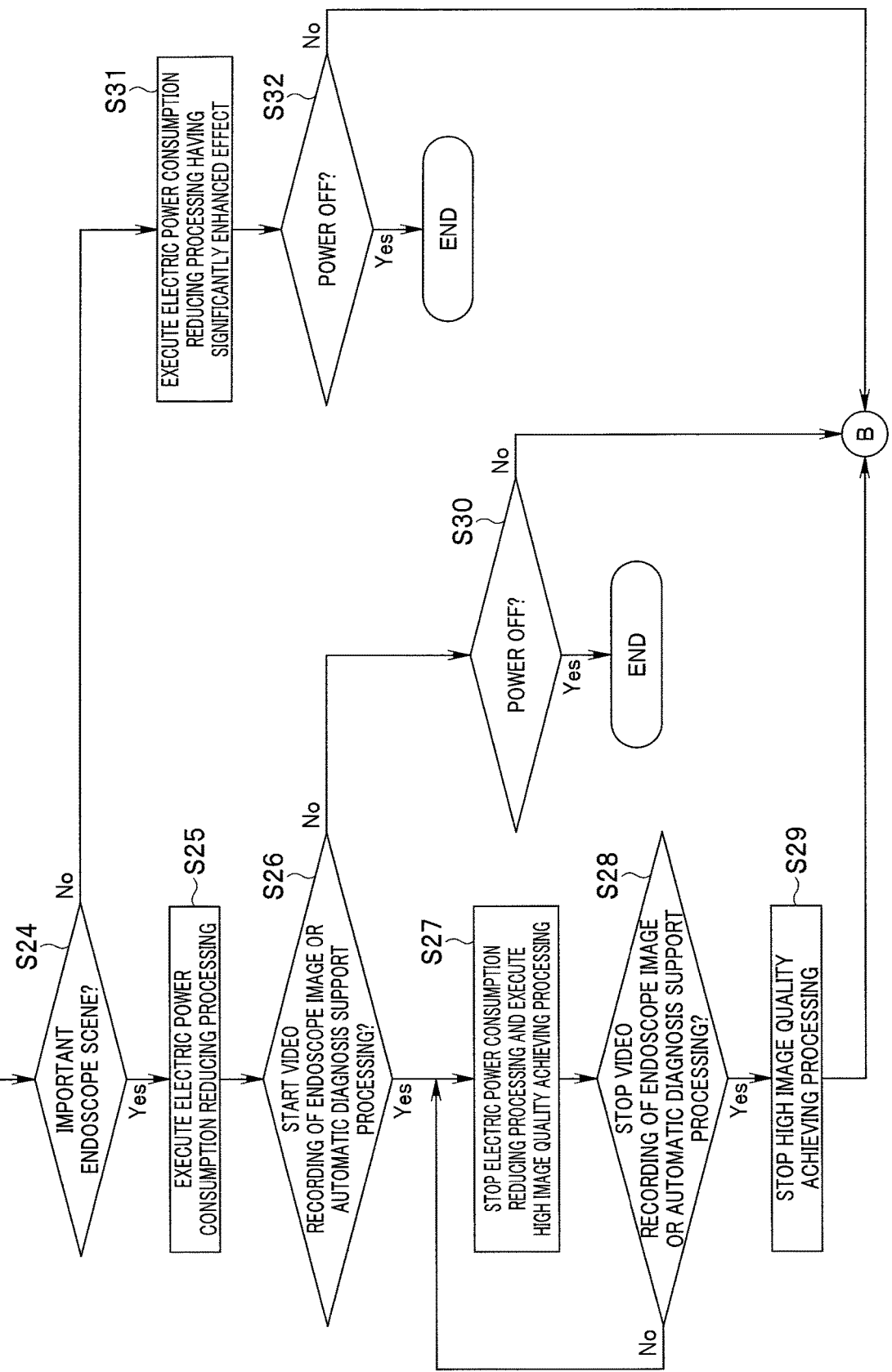
FIG. 6 is a flowchart illustrating other part of the operation of the endoscope system according to the first embodiment of the present invention.

Subsequently, a specific example of a series of operations related to the parameter control device 5 in operation of the endoscope system 1 will be described below with reference to FIGS. 2, 3, 5 and 6. FIG. 5 is a flowchart illustrating part of the operation of the endoscope system 1. FIG. 6 is a flowchart illustrating the other part of the operation of the endoscope system 1.

As illustrated in FIG. 5, first in the series of operations, an operation signal that activates the endoscope system 1 is inputted from the user IF unit 39 to the main control unit 38 as, for example, the user operates a switch or the like for activating the endoscope system 1. The main control unit 38 activates the endoscope system 1 based on the inputted operation signal (step S11). Subsequently, wireless communication connection is established between the endoscope 2 and the video processor 3 as the main control unit of the endoscope 2 controls the first wireless communication unit 24A and the main control unit 38 of the video processor 3 controls the second wireless communication unit 31A (step S12).

Subsequently, the illumination light source is powered on as the main control unit of the endoscope 2 controls the illumination unit 22 (step S13), and the endoscope 2 and the video processor 3 start execution of the standard processing. Subsequently, the user starts an insertion operation that inserts the insertion portion 2A of the endoscope 2 into a body of a patient (step S14).

Subsequently, the data collection unit 51 of the parameter control device 5 acquires a plurality of pieces of information related to the endoscope system 1 (step S15). Subsequently, the determination unit 52 of the parameter control device 5 determines the information related to the remaining amount of the battery 25A (step S16). When the determination unit 52 determines that the remaining amount of the battery 25A is smaller than the predetermined battery threshold value (Yes), step S24 in FIG. 6 is executed.

When the determination unit 52 determines that the remaining amount of the battery 25A is not smaller than the predetermined battery threshold value at step S16 (No), in other words, when the remaining amount of the battery 25A is equal to or larger than the predetermined battery threshold value, the determination unit 52 subsequently determines the information related to the temperature of the grasping portion 2Ba (step S17). When the determination unit 52 determines that the temperature of the grasping portion 2Ba is equal to or higher than the predetermined temperature threshold value (Yes), step S24 in FIG. 6 is executed.

When the determination unit 52 determines that the temperature of the grasping portion 2Ba is not equal to nor higher than the predetermined temperature threshold value at step S17 (No), in other words, when the temperature of the grasping portion 2Ba is lower than the predetermined temperature threshold value, the determination unit 52 subsequently determines whether to start the video recording of the endoscope image or the automatic diagnosis support processing (step S18). When the determination unit 52 determines to start the video recording of the endoscope image or the automatic diagnosis support processing (Yes), the determination unit 52 determines to execute the high image quality achieving processing. Accordingly, the high image quality achieving processing is executed (step S19). The execution of the high image quality achieving processing is achieved when the determination unit 52 determines to execute the high image quality achieving processing, and then the parameter determination unit 53 of the parameter control device 5 determines the illumination parameter, the compression parameter, and the first and second brightness parameters for executing the high image quality achieving processing as described above, and the parameter transmission unit 54 of the parameter control device 5 executes processing that transmits these parameters. A setting example of the parameters will be described later.

Subsequently in the series of operations, the determination unit 52 determines whether to stop the video recording of the endoscope image or the automatic diagnosis support processing (step S20). This determination may be performed based on, for example, first to fourth conditions below. The first condition is such that the information for stopping the video recording of the endoscope image or the information for stopping the automatic diagnosis support processing is acquired. The second condition is such that an execution time of the video recording of the endoscope image or the automatic diagnosis support processing exceeds a predetermined time. The third condition is such that the remaining amount of the battery 25A is smaller than a predetermined battery threshold value. The fourth condition is such that the temperature of the grasping portion 2Ba is equal to or higher than a predetermined temperature threshold value. The determination unit 52 may determine to stop the video recording of the endoscope image or the automatic diagnosis support processing when at least one of the first to fourth conditions is satisfied.

Note that the battery threshold value in the third condition may be the same as or different from the battery threshold value at step S16. Similarly, the temperature threshold value in the fourth condition may be the same as or different from the temperature threshold value at step S17.

When the determination unit 52 does not determine to stop the video recording of the endoscope image or the automatic diagnosis support processing at step S20 (No), step S19 is executed again to continuously execute the high image quality achieving processing. When the determination unit 52 determines to stop the video recording of the endoscope image or the automatic diagnosis support processing at step S20 (Yes), the determination unit 52 determines to stop the high image quality achieving processing. Accordingly, the high image quality achieving processing is stopped (step S21). The stop of the high image quality achieving processing is achieved when the determination unit 52 determines to stop the high image quality achieving processing, and then the parameter determination unit 53 sets each parameter back to a parameter used in the standard processing, and the parameter transmission unit 54 executes processing that transmits each parameter.

Subsequently in the series of operations, for example, the main control unit 38 determines whether to power off the endoscope system 1 (step S22). Specifically, the main control unit 38 determines whether an operation signal that powers off the endoscope system 1 is inputted. The operation signal is inputted from the user IF unit 39 to the main control unit 38 as, for example, the user operates a switch or the like for powering off the endoscope system 1. When the operation signal is not inputted to the main control unit 38, the main control unit 38 determines not to power off the endoscope system 1 (No), and step S15 is executed again. When the operation signal is inputted to the main control unit 38, the main control unit 38 determines to power off the endoscope system 1 (Yes), and the series of operations are ended.

When the determination unit 52 does not determine to start the video recording of the endoscope image or the automatic diagnosis support processing at step S18 (No), for example, the main control unit 38 subsequently determines whether to power off the endoscope system 1 (step S23). Contents of step S23 are the same as contents of step S22. When the main control unit 38 does not determine to power off the endoscope system 1 (No), step S15 is executed again. When the main control unit 38 determines to power off the endoscope system 1 (Yes), the series of operations are ended.

Note that, in a case in which step S15 is executed again after step S23, when the determination unit 52 determines to execute the electric power consumption reducing processing at a step to be described later and each parameter is set to a parameter used in the electric power consumption reducing processing, step S15 is executed again after the parameter determination unit 53 sets each parameter back to a parameter used in the standard processing and the parameter transmission unit 54 executes processing that transmits each parameter.

As illustrated in FIG. 6, when the remaining amount of the battery 25A is smaller than the predetermined battery threshold value at step S16 in FIG. 5 or when the temperature of the grasping portion 2Ba is equal to or higher than the predetermined temperature threshold value at step S17 in FIG. 5, the determination unit 52 subsequently determines the information related to an endoscope scene (step S24). When the determination unit 52 determines that the endoscope scene is an important endoscope scene, such as the detailed-check scene, which needs the endoscope image of high resolution (Yes), the determination unit 52 subsequently determines to execute the electric power consumption reducing processing (step S25). The execution of the electric power consumption reducing processing is achieved when the determination unit 52 determines to execute the electric power consumption reducing processing, and then the parameter determination unit 53 determines the illumination parameter, the compression parameter, and the first and second brightness parameters as described above and the parameter transmission unit 54 executes processing that transmits these parameters. A setting example of the parameters will be described later.

Subsequently in the series of operations, the determination unit 52 determines whether to start the video recording of the endoscope image or the automatic diagnosis support processing (step S26). When the determination unit 52 determines to start the video recording of the endoscope image or the automatic diagnosis support processing (Yes), the determination unit 52 determines to stop the electric power consumption reducing processing and execute the high image quality achieving processing. Accordingly, the high image quality achieving processing is executed (step S27). Contents of step S27 are basically the same as contents of step S19 in FIG. 5. Note that the stop of the electric power consumption reducing processing and the execution of the high image quality achieving processing are achieved when the parameter determination unit 53 determines the illumination parameter, the compression parameter, and the first and second brightness parameters for executing the high image quality achieving processing and the parameter transmission unit 54 executes processing that transmits these parameters.

Subsequently in the series of operations, the determination unit 52 determines whether to stop the video recording of the endoscope image or the automatic diagnosis support processing (step S28). Contents of step S28 are the same as contents of step S20 in FIG. 5. When the determination unit 52 does not determine to stop the video recording of the endoscope image or the automatic diagnosis support processing (No), step S27 is executed again to continuously execute the high image quality achieving processing. When the determination unit 52 determines to stop the video recording of the endoscope image or the automatic diagnosis support processing (Yes), the determination unit 52 determines to stop the high image quality achieving processing. Accordingly, the high image quality achieving processing is stopped (step S29). The stop of the high image quality achieving processing is achieved when the determination unit 52 determines to stop the high image quality achieving processing, and then the parameter determination unit 53 sets each parameter back to a parameter before the execution of the high image quality achieving processing, and the parameter transmission unit 54 executes processing that transmits each parameter. Subsequently, step S15 in FIG. 5 is executed again.

When the determination unit 52 does not determine to start the video recording of the endoscope image or the automatic diagnosis support processing at step S26 (No), for example, the main control unit 38 subsequently determines whether to power off the endoscope system 1 (step S30). Contents of step S30 are the same as the contents of step S22 in FIG. 5. When the main control unit 38 does not determine to power off the endoscope system 1 (No), step S15 in FIG. 5 is executed again. When the main control unit 38 determines to power off the endoscope system 1 (Yes), the series of operations are ended.

When the determination unit 52 determines that the endoscope scene is not important at step S24 (No), the determination unit 52 subsequently determines to execute the electric power consumption reducing processing having a significantly enhanced effect. Accordingly, the electric power consumption reducing processing having a significantly enhanced effect is executed (step S31). The execution of the electric power consumption reducing processing having a significantly enhanced effect is achieved when the parameter determination unit 53 determines the illumination parameter so that the illumination light amount is smaller than in the normal electric power consumption reducing processing, determines the compression parameter so that the data amount of the compressed data is smaller than in the normal electric power consumption reducing processing, determines the first brightness parameter so that the effect of the filter processing is stronger than in the normal electric power consumption reducing processing, and determines the second brightness parameter so that the effect of the multiplication processing is stronger than in the normal electric power consumption reducing processing, and the parameter transmission unit 54 executes processing that transmits these parameters.

Subsequently in the series of operations, for example, the main control unit 38 determines whether to power off the endoscope system 1 (step S32). Contents of step S32 are the same as the contents of step S22 in FIG. 5. When the main control unit 38 does not determine to power off the endoscope system 1 (No), step S15 in FIG. 5 is executed again.

When the main control unit 38 determines to power off the endoscope system 1 (Yes), the series of operations are ended.

(Setting Example of Parameters)

Subsequently, a setting example of the parameters will be described below. In this example, the illumination parameter, the compression parameter, the first brightness parameter, and the second brightness parameter are each expressed by using a value of one to five inclusive. It is set that the illumination light amount is largest when the value of the illumination parameter is one, and the illumination light amount is smallest when the value is five. In other words, it is set that an effect of the electric power consumption reducing processing is weakest when the value of the illumination parameter is one, and the effect of the electric power consumption reducing processing is strongest when the value is five.

It is set that the compression ratio is lowest when the value of the compression parameter is one, and the compression ratio is highest when the value is five. In other words, the effect of the electric power consumption reducing processing is weakest when the value of the compression parameter is one, and the effect of the electric power consumption reducing processing is strongest when the value is five.

It is set that the effect of the filter processing is weakest when the value of the first brightness parameter is one, and the effect of the filter processing is strongest when the value is five. It is set that the effect of the multiplication processing is weakest when the value of the second brightness parameter is one, and the effect of the multiplication processing is strongest when the value is five. Brightness of a correction target pixel is lowest when the effect of the filter processing or the multiplication processing is weakest, and is highest when the effect of the filter processing or the multiplication processing is strongest.

Hereinafter, default values are defined to be the values of the parameters when either the electric power consumption reducing processing or the high image quality achieving processing is not executed and the endoscope scene is the detailed-check scene. The default values are three. First, a setting example of the parameters when either the electric power consumption reducing processing or the high image quality achieving processing is not executed, in other words, when the standard processing is executed will be described with reference to Table 1. Table 1 presents the setting example of the parameters when the standard processing is executed and the endoscope scene is the detailed-check scene, the screening scene, and the external scene.

TABLE 1

| Parameter | Detailed-check scene | Screening scene | External scene |
|---|---|---|---|
| Illumination parameter | 3 | 4 | 5 |
| Compression parameter | 3 | 4 | 5 |
| First brightness parameter | 3 | 4 | 5 |
| Second brightness parameter | 3 | 4 | 5 |

The illumination parameter, the compression parameter, the first brightness parameter, and the second brightness parameter are set so that the image quality and the resolution of the endoscope image are at predetermined levels when the standard processing is executed and the endoscope scene is the detailed-check scene. In the external scene, the image quality and the resolution of the endoscope image may be low. Thus, in the external scene, the illumination parameter and the compression parameter are set so that consumption of electric power of the battery 25A is smallest, and the first and second brightness parameters are set in accordance with the setting of the illumination parameter and the compression parameter. In the screening scene, the image quality and the resolution of the endoscope image are higher than in the external scene, but the illumination parameter, the compression parameter, the first brightness parameter, and the second brightness parameter are set so that consumption of electric power of the battery 25A is smaller than in the detailed-check scene.

Subsequently, a setting example of the parameters when the electric power consumption reducing processing and the high image quality achieving processing are executed will be described with reference to Table 2. In the present embodiment, the normal electric power consumption reducing processing (step S25) and the electric power consumption reducing processing having a significantly enhanced effect (step S31) are executed as the electric power consumption reducing processing. Table 2 presents the setting example of the parameters when the two kinds of the electric power consumption reducing processing and the high image quality achieving processing are executed.

TABLE 2

| Parameter | Electric power consumption reducing processing (step S25) | Electric power consumption reducing processing (step S31) | High image quality achieving processing |
|---|---|---|---|
| Illumination parameter | 3.5 | 4 | 2 |
| Compression parameter | 3.5 | 4 | 2 |
| First brightness parameter | 3.5 | 3.25 | 2 |
| Second brightness parameter | 3.5 | 4 | 2 |

The normal electric power consumption reducing processing (step S25) is executed when the determination unit 52 determines that the endoscope scene is an important scene. In this case, the parameters are set so that the endoscope image of high image quality and high resolution can be obtained despite of the execution of the electric power consumption reducing processing. Specifically, the illumination parameter is set to a value (in Table 2, 3.5) with which the illumination light amount of the illumination unit 22 is smaller than when the electric power consumption reducing processing is not executed. The compression parameter is set to a value (in Table 2, 3.5) with which the compression ratio is higher, in other words, the data amount of the compressed data is smaller than when the electric power consumption reducing processing is not executed. The first brightness parameter is set to a value (in Table 2, 3.5) with which the effect of the filter processing is stronger than when the electric power consumption reducing processing is not executed. The second brightness parameter is set to a value (in Table 2, 3.5) with which the effect of the multiplication processing is stronger than when the electric power consumption reducing processing is not executed.

The electric power consumption reducing processing having a significantly enhanced effect (step S31) is executed when the determination unit 52 determines that the endoscope scene is not an important scene. In this case, the parameters are set so that the endoscope image of minimum image quality and resolution with which, for example, the insertion portion 2A can be removed out of the body can be obtained despite of enhancement of the effect of the electric power consumption reducing processing. Specifically, the illumination parameter is set to a value (in Table 2, 4) with which the illumination light amount of the illumination unit 22 is significantly smaller than when the electric power consumption reducing processing is not executed. The compression parameter is set to a value (in Table 2, 4) with which the compression ratio is significantly higher, in other words, the data amount of the compressed data is significantly smaller than when the electric power consumption reducing processing is not executed. The first brightness parameter is set to a value (in Table 2, 3.25) with which the effect of the filter processing is slightly stronger than when the electric power consumption reducing processing is not executed. The second brightness parameter is set to a value (in Table 2, 4) with which the effect of the multiplication processing is significantly stronger than when the electric power consumption reducing processing is not executed.

When the high image quality achieving processing is executed, the parameters are set so that the endoscope image of higher image quality than when the high image quality achieving processing is not executed can be obtained. Specifically, the illumination parameter is set to a value (in Table 2, 2) with which the illumination light amount of the illumination unit 22 is larger than when the high image quality achieving processing is not executed. The compression parameter is set to a value (in Table 2, 2) with which the compression ratio is lower, in other words, the data amount of the compressed data is larger than when the high image quality achieving processing is not executed. The first brightness parameter is set to a value (in Table 2, 2) with which the effect of the filter processing is weaker than when the high image quality achieving processing is not executed. The second brightness parameter is set to a value (in Table 2, 2) with which the effect of the multiplication processing is weaker than when the electric power consumption reducing processing is not executed.

(Operations and Effects)

Subsequently, operations and effects of the endoscope system 1 and the parameter control device 5 according to the present embodiment will be described below. In the present embodiment, during execution of the electric power consumption reducing processing, when the data collection unit 51 acquires at least one of the information for starting the video recording of the endoscope image or the information for starting the automatic diagnosis support processing, the determination unit 52 determines to stop the electric power consumption reducing processing and execute the high image quality achieving processing. Specifically, in the present embodiment, when the high image quality achieving processing needs to be executed during execution of the electric power consumption reducing processing, temporary continuation of higher consumption of electric power of the battery 25A and higher temperature of the grasping portion 2Ba is allowed during the execution of the high image quality achieving processing. With this configuration, according to the present embodiment, even when the electric power consumption reducing processing is executed, it is possible to achieve high image quality of an endoscope image video-recorded by the video recording processing and achieve high image quality of an endoscope image used in the automatic diagnosis support processing, thereby improving the accuracy of automatic diagnosis.

Note that, in the present embodiment, when the high image quality achieving processing is executed, the compression parameter is set to a value with which the compression ratio is lower, in other words, the data amount of the compressed data is larger than when the high image quality achieving processing is not executed, the first brightness parameter is set to a value with which the effect of the filter processing is weaker than when the high image quality achieving processing is not executed, and the second brightness parameter is set to a value with which the effect of the multiplication processing is weaker than when the electric power consumption reducing processing is not executed. With this configuration, according to the present embodiment, resolution decrease and noise increase can be prevented to further improve the image quality of the endoscope image.

Second Embodiment

Figure 7:
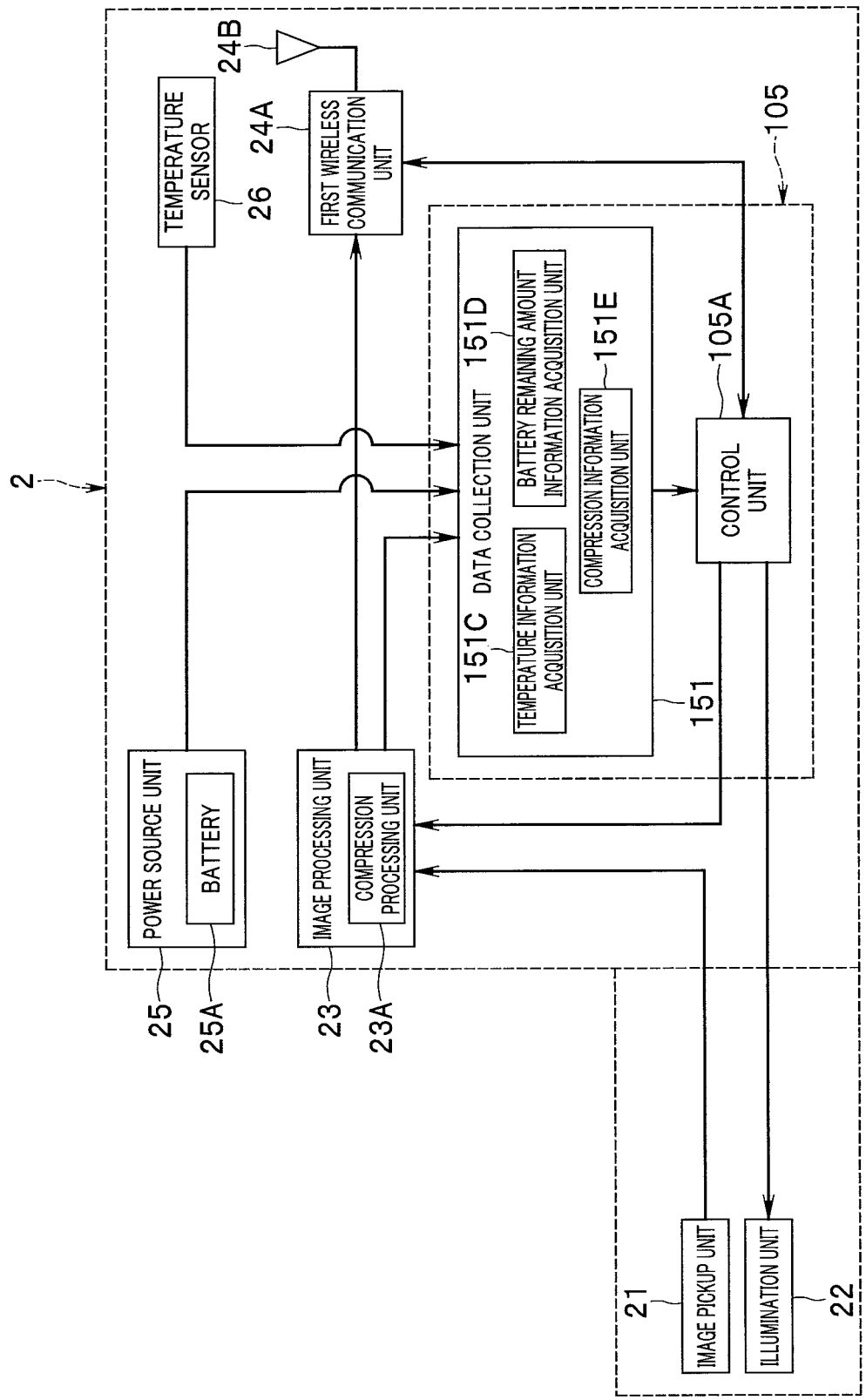
FIG. 7 is a functional block diagram illustrating configurations of an endoscope and a first part of a parameter control device in an endoscope system according to a second embodiment of the present invention.
Figure 8:
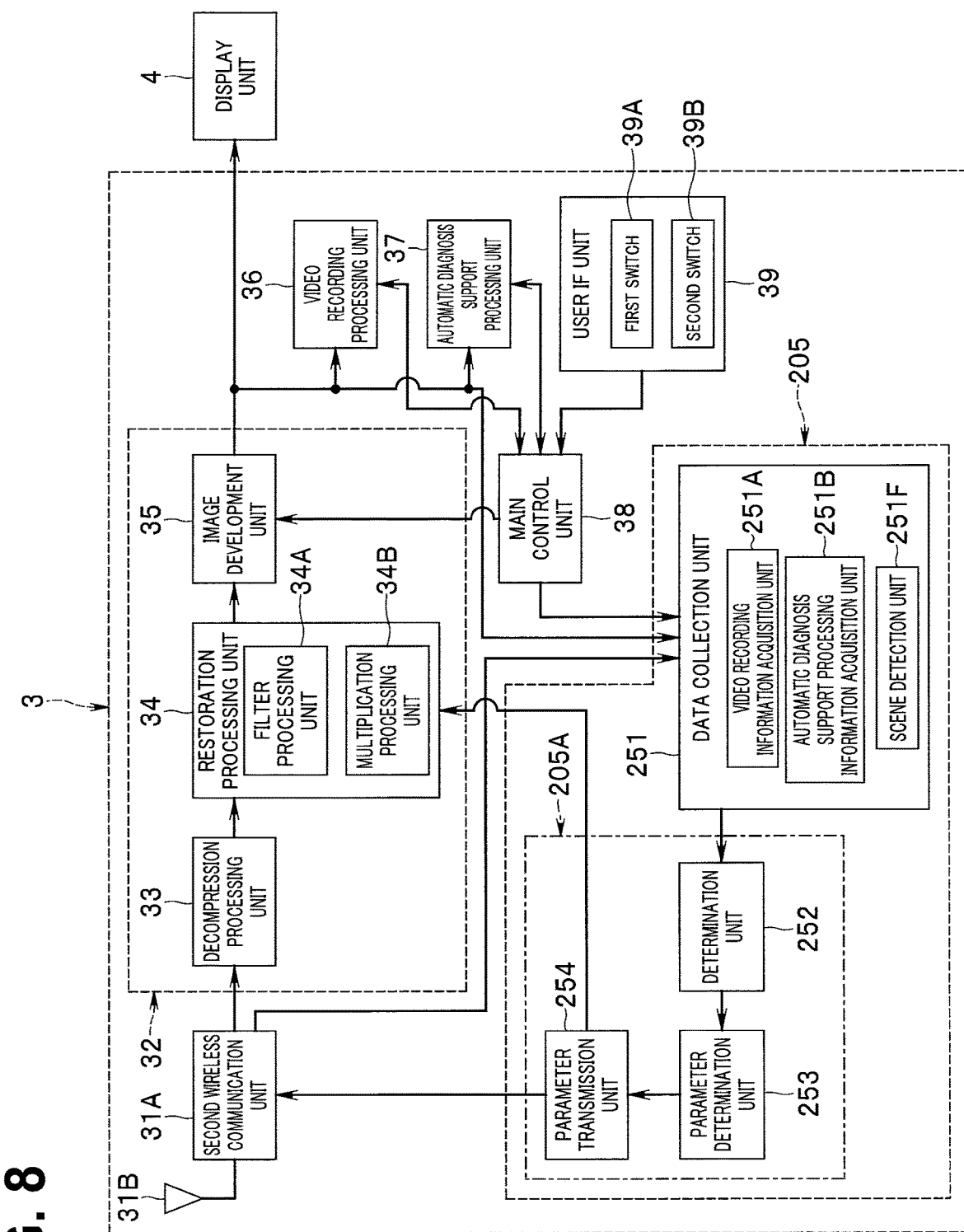
FIG. 8 is a functional block diagram illustrating configurations of the video processor and a second part of the parameter control device in the endoscope system according to the second embodiment of the present invention.

Subsequently, an endoscope system according to a second embodiment of the present invention will be described below with reference to FIGS. 7 and 8. FIG. 7 is a functional block diagram illustrating a configuration of an endoscope and a first part of a parameter control device in the endoscope system according to the present embodiment. FIG. 8 is a functional block diagram illustrating a configuration of a video processor and a second part of the parameter control device in the endoscope system according to the present embodiment.

A configuration of the endoscope system according to the present embodiment is different from the configuration of the endoscope system 1 according to the first embodiment as follows. As illustrated in FIGS. 7 and 8, the endoscope system according to the present embodiment includes the parameter control device according to the present embodiment in place of the parameter control device 5 according to the first embodiment. The parameter control device according to the present embodiment includes a first part 105 provided in the endoscope 2, and a second part 205 provided in the video processor 3.

As illustrated in FIG. 7, the first part 105 of the parameter control device includes a data collection unit 151 and a control unit 105A. The data collection unit 151 includes a temperature information acquisition unit 151C, a battery remaining amount information acquisition unit 151D, and a compression information acquisition unit 151E. In other words, the temperature information acquisition unit 151C and the battery remaining amount information acquisition unit 151D are provided in the endoscope 2. Functions of the temperature information acquisition unit 151C, the battery remaining amount information acquisition unit 151D, and the compression information acquisition unit 151E are the same as functions of the temperature information acquisition unit 51C, the battery remaining amount information acquisition unit 51D, and the compression information acquisition unit 51E, respectively, in the first embodiment.

The data collection unit 151 outputs, to the control unit 105A, information related to the temperature of the grasping portion 2Ba, which is acquired by the temperature information acquisition unit 151C, information related to the remaining amount of the battery 25A, which is acquired by the battery remaining amount information acquisition unit 151D, and information related to the compression processing, which is acquired by the compression information acquisition unit 151E. The control unit 105A outputs the plurality of pieces of information acquired by the data collection unit 151 to the second part 205 of the parameter control device through wireless communication between the endoscope 2 and the video processor 3.

As illustrated in FIG. 8, the second part 205 of the parameter control device includes a data collection unit 251, a determination unit 252, a parameter determination unit 253, and a parameter transmission unit 254. The determination unit 252, the parameter determination unit 253, and the parameter transmission unit 254 are included in a control unit 205A as a main part of the parameter control device. In other words, the determination unit 252 and the parameter determination unit 253 are provided in the video processor 3.

The data collection unit 251 includes a video recording information acquisition unit 251A, an automatic diagnosis support processing information acquisition unit 251B, and a scene detection unit 251F. In other words, the video recording information acquisition unit 251A and the automatic diagnosis support processing information acquisition unit 251B are provided in the video processor 3.

Functions of the video recording information acquisition unit 251A and the automatic diagnosis support processing information acquisition unit 251B are basically the same as functions of the video recording information acquisition unit 51A and the automatic diagnosis support processing information acquisition unit 51B, respectively, in the first embodiment. Note that, in the present embodiment, the main control unit 38 of the video processor 3 outputs, to the data collection unit 251, information for starting or stopping the video recording of the endoscope image and information for starting or stopping the automatic diagnosis support processing. Accordingly, the video recording information acquisition unit 251A can acquire the information for starting or stopping the video recording of the endoscope image, and the automatic diagnosis support processing information acquisition unit 251B can acquire the information for starting or stopping the automatic diagnosis support processing.

Functions of the scene detection unit 251F are basically the same as functions of the scene detection unit 51F in the first embodiment. Note that, in the present embodiment, the image processing unit 32 outputs, as information related to an endoscope scene, image data for detecting an endoscope scene to the second part 205 of the parameter control device. In an example illustrated in FIG. 8, the scene detection unit 251F receives the endoscope image outputted from the image development unit 35 of the image processing unit 32. The scene detection unit 251F detects an endoscope scene by analyzing acquired image data, in other words, the endoscope image.

The data collection unit 251 receives a plurality of pieces of information collected by the data collection unit 151 and outputted from the control unit 105A. Accordingly, the data collection unit 251 acquires the plurality of pieces of information acquired by the data collection unit 151 in effect.

The determination unit 252 performs, based on the plurality of pieces of information acquired by the data collection unit 251 (including the plurality of pieces of information acquired by the data collection unit 151), determination of whether to execute or stop the electric power consumption reducing processing and determination of whether to execute or stop the high image quality achieving processing. A method of determination of whether to execute or stop the electric power consumption reducing processing and a method of determination of whether to execute or stop the high image quality achieving processing are the same as in the first embodiment.

The parameter determination unit 253 determines one or more parameters used in processing that the determination unit 252 determines to execute. A method of the parameter determination is the same as in the first embodiment.

The parameter transmission unit 254 transmits the plurality of parameters determined by the parameter determination unit 253 to components of the endoscope 2 and the video processor 3. Specifically, the parameter transmission unit 254 transmits the illumination parameter and the compression parameter to the control unit 105A, transmits the first brightness parameter to the filter processing unit 34A of the restoration processing unit 34, and transmits the second brightness parameter to the multiplication processing unit 34B of the restoration processing unit 34. The control unit 105A outputs the received illumination parameter to the illumination unit 22 and outputs the received compression parameter to the compression processing unit 23A.

In the present embodiment, the control unit 205A as the main part of the parameter control device is provided in the video processor 3. With this configuration, according to the present embodiment, consumption of electric power of the battery 25A can be reduced as compared to a configuration the main part of the parameter control device is provided in the endoscope 2.

Other configurations, operations, and effects in the present embodiment are the same as in the first embodiment.

Third Embodiment

Figure 9:
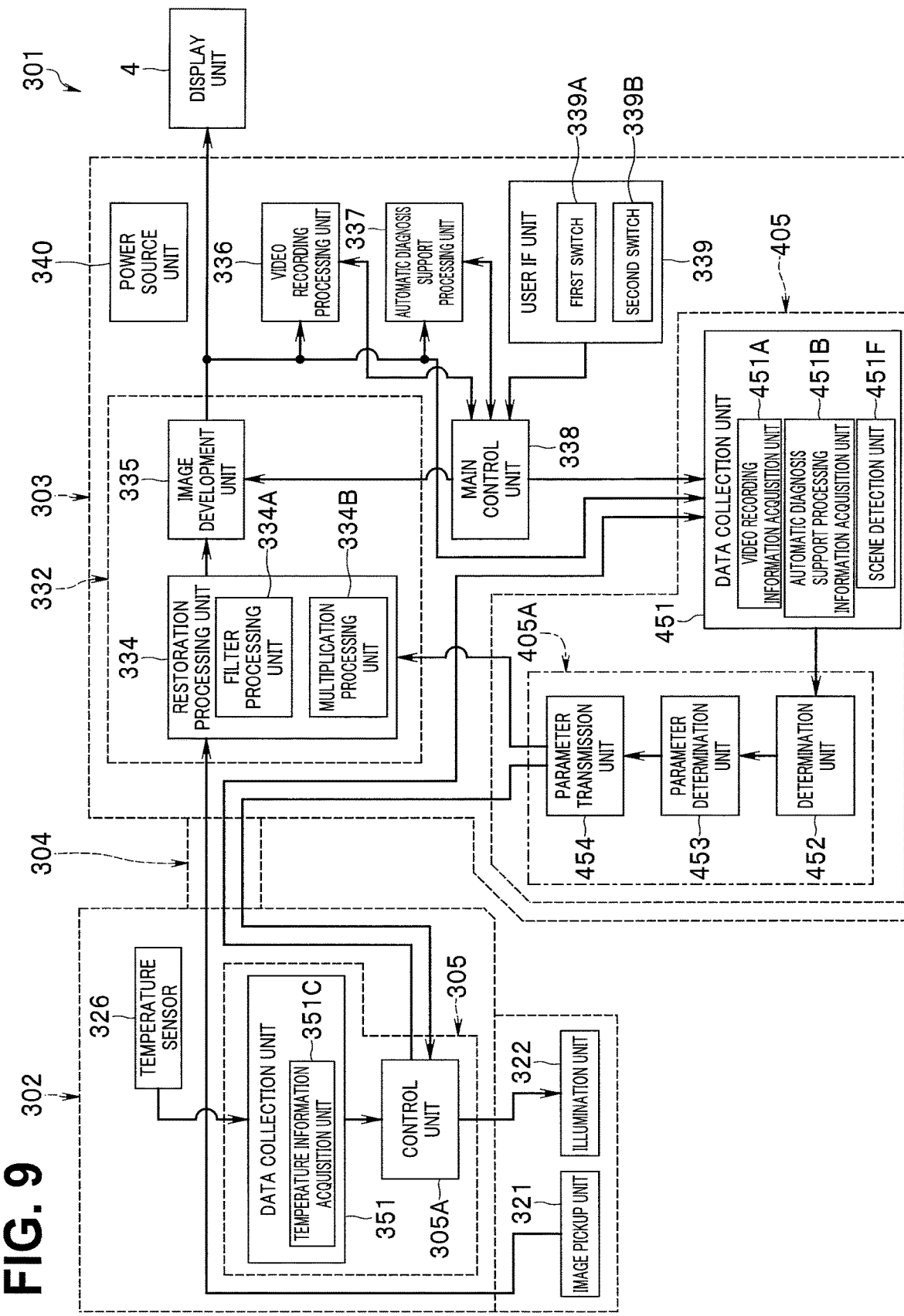
FIG. 9 is a functional block diagram illustrating a configuration of an endoscope system according to a third embodiment of the present invention.

Subsequently, an endoscope system according to a third embodiment of the present invention will be described below with reference to FIG. 9. FIG. 9 is a functional block diagram illustrating a configuration of the endoscope system according to the present embodiment. The endoscope system 301 according to the present embodiment includes an endoscope 302, a video processor 303, a universal cable 304 connecting the endoscope 302 and the video processor 303, and a display unit 4 connected to the video processor 303. A configuration of the display unit 4 is the same as in the first embodiment.

Although not illustrated, the endoscope 302 includes an elongated insertion portion that is inserted into a body cavity, and an operation portion including a grasping portion that is grasped by a user. The operation portion is provided at a proximal end portion of the insertion portion. The universal cable 304 extends from the operation portion.

The endoscope 302 further includes an image pickup unit 321 configured to generate image data through image pickup of an object, and an illumination unit 322 configured to illuminate the object. Similarly to the image pickup unit 21 in the first embodiment, the image pickup unit 321 includes an image pickup device provided at a distal end portion of the insertion portion. Similarly to the illumination unit 22 in the first embodiment, the illumination unit 322 includes an illumination light source, and a lens provided at a distal end of the insertion portion.

The endoscope system 301 further includes a power source unit 340 and a parameter control device according to the present embodiment. The parameter control device is a device configured to cause the endoscope 302 and the video processor 303 to execute predetermined processing by controlling a plurality of parameters used in the endoscope 302 and the video processor 303. The parameter control device includes a first part 305 provided in the endoscope 302, and a second part 405 provided in the video processor 303.

The endoscope 302 further includes a temperature sensor 326. The temperature sensor 326 is able to measure temperature of the grasping portion, and outputs a measurement result of the temperature of the grasping portion to the first part 305 of the parameter control device.

The first part 305 of the parameter control device includes a data collection unit 351 and a control unit 305A. The data collection unit 351 includes a temperature information acquisition unit 351C. Functions of the temperature information acquisition unit 351C are the same as functions of the temperature information acquisition unit 51C in the first embodiment.

The data collection unit 351 outputs, to the control unit 305A, information related to the temperature of the grasping portion, which is acquired by the temperature information acquisition unit 351C. The control unit 305A outputs a plurality of pieces of information acquired by the data collection unit 351 to the second part 405 of the parameter control device.

The endoscope 302 further includes a non-illustrated main control unit. The main control unit controls each component in the endoscope 302 including the first part 305 of the parameter control device.

The video processor 303 includes a processor image processing unit (hereinafter simply referred to as an image processing unit) 332, a video recording processing unit 336, an automatic diagnosis support processing unit 337, a main control unit 338, and a user IF unit 339. Functions of the video recording processing unit 336 and the automatic diagnosis support processing unit 337 are the same as functions of the video recording processing unit 36 and the automatic diagnosis support processing unit 37, respectively, in the first embodiment.

The image processing unit 332 generates an endoscope image by performing predetermined image processing to image data generated by the image pickup unit 321. In the present embodiment, the image processing unit 332 includes a restoration processing unit 334 and an image development unit 335. Functions of the restoration processing unit 334 and the image development unit 335 are the same as functions of the restoration processing unit 34 and the image development unit 35, respectively, in the first embodiment. The image processing unit 332 outputs the endoscope image generated by the image development unit 335 to the video recording processing unit 336, the automatic diagnosis support processing unit 337, and the display unit 4.

A configuration of the restoration processing unit 334 is the same as a configuration of the restoration processing unit 34 in the first embodiment. Specifically, the restoration processing unit 334 includes a filter processing unit 334A and a multiplication processing unit 334B. Functions of the filter processing unit 334A and the multiplication processing unit 334B are the same as functions of the filter processing unit 34A and the multiplication processing unit 34B, respectively, in the first embodiment.

A configuration and functions of the user IF unit 339 are basically the same as a configuration and functions of the user IF unit 39 in the first embodiment. Note that, in the present embodiment, the user IF unit 339 includes a first switch 339A and a second switch 339B. Functions of the first switch 339A and the second switch 339B are the same as functions of the first switch 39A and the second switch 39B, respectively, in the first embodiment.

The power source unit 340 is provided in the video processor 303 and supplies electric power to each component of the endoscope 302 and the video processor 303, including the image pickup unit 321 and the illumination unit 322 of the endoscope 302.

The main control unit 338 controls each component in the video processor 303, and also controls the power source unit 340 to supply power to each component in the endoscope 302 and the video processor 303. The main control unit 338 outputs information based on an operation signal inputted from the user IF unit 339, to each component of the endoscope 302 and the video processor 303 and to the second part 405 of the parameter control device. Accordingly, the main control unit 338 can provide various instructions based on the operation signal, to each component of the endoscope 302, the video processor 303, and the second part 405 of the parameter control device.

Similarly to the main control unit 38 in the first embodiment, the main control unit 338 generates, based on an operation signal that instructs start or stop of video recording of the endoscope image, information for starting the video recording of the endoscope image and information for stopping the video recording of the endoscope image, and outputs these pieces of information to the video recording processing unit 336 and the second part 405 of the parameter control device. In addition, the main control unit 338 generates, based on an operation signal that instructs start or stop of the automatic diagnosis support processing, information for starting automatic diagnosis support processing and information for stopping the automatic diagnosis support processing, and outputs these pieces of information to the automatic diagnosis support processing unit 337 and the second part 405 of the parameter control device.

The second part 405 of the parameter control device includes a data collection unit 451, a determination unit 452, a parameter determination unit 453, and a parameter transmission unit 454. The determination unit 452, the parameter determination unit 453, and the parameter transmission unit 454 are included in a control unit 405A as a main part of the parameter control device.

The data collection unit 451 includes a video recording information acquisition unit 451A, an automatic diagnosis support processing information acquisition unit 451B, and a scene detection unit 451F. Functions of the video recording information acquisition unit 451A and the automatic diagnosis support processing information acquisition unit 451B are basically the same as functions of the video recording information acquisition unit 51A and the automatic diagnosis support processing information acquisition unit 51B, respectively, in the first embodiment.

Functions of the scene detection unit 451F are basically the same as functions of the scene detection unit 51F in the first embodiment. Note that, in the present embodiment, the image processing unit 332 outputs, as information related to an endoscope scene, image data for detecting an endoscope scene to the second part 405 of the parameter control device. In an example illustrated in FIG. 9, the scene detection unit 451F receives the endoscope image outputted from the image development unit 335 of the image processing unit 332. The scene detection unit 451F detects an endoscope scene by analyzing acquired image data, in other words, the endoscope image.

In addition, the data collection unit 451 receives information collected by the data collection unit 351 and outputted from the control unit 305A. Accordingly, the data collection unit 451 also acquires the information acquired by the data collection unit 351 in effect.

The determination unit 452 performs, based on the plurality of pieces of information acquired by the data collection unit 451 (including the information acquired by the data collection unit 351), determination of whether to execute or stop the electric power consumption reducing processing and determination of whether to execute or stop the high image quality achieving processing. The method of determination of whether to execute or stop the electric power consumption reducing processing and the method of determination of whether to execute or stop the high image quality achieving processing are basically the same as in the first embodiment. Note that, in the present embodiment, determination of whether to execute the electric power consumption reducing processing is performed by using only the information related to the temperature of the grasping portion, which is acquired by the temperature information acquisition unit 351C. The determination unit 452 determines to execute the electric power consumption reducing processing when the temperature of the grasping portion is equal to or higher than a predetermined temperature threshold value.

The parameter determination unit 453 determines one or more parameters used in processing that the determination unit 452 determines to execute. A method of the parameter determination is the same as in the first embodiment.

The parameter transmission unit 454 transmits a plurality of parameters determined by the parameter determination unit 453 to components of the endoscope 302 and the video processor 303. Specifically, the parameter transmission unit 454 transmits the illumination parameter to the control unit 305A, transmits the first brightness parameter to the filter processing unit 334A of the restoration processing unit 334, and transmits the second brightness parameter to the multiplication processing unit 334B of the restoration processing unit 334. The control unit 305A outputs the received illumination parameter to the illumination unit 322.

Note that a hardware configuration of the endoscope system 301 may be the same as the hardware configuration of the endoscope system 1 according to the first embodiment. Note that, in the present embodiment, in particular, signal transmission and reception performed between the endoscope 302 and the video processor 303 are performed through the universal cable 304.

In the present embodiment, the high image quality achieving processing includes illumination light amount change processing that changes an illumination light amount of the illumination unit 322 and brightness correction processing performed by the restoration processing unit 334. Contents of the illumination light amount change processing and the brightness correction processing of the high image quality achieving processing are the same as in the first embodiment.

In the present embodiment, the electric power consumption reducing processing is processing that reduces electric power supplied from the power source unit 340. The electric power consumption reducing processing includes the illumination light amount change processing and the brightness correction processing. Contents of the illumination light amount change processing and the brightness correction processing of the electric power consumption reducing processing are the same as in the first embodiment.

Other configurations, operations, and effects in the present embodiment are the same as in the first embodiment.

The present invention is not limited to the above-described embodiments but may be provided with various kinds of changes, modifications, and the like without changing the gist of the present invention. For example, each parameter control device of the present invention may be a device separated from the endoscope and the video processor.

In the first and second embodiments, the video recording information acquisition unit, the automatic diagnosis support processing information acquisition unit, and the scene detection unit of each data collection unit may be provided in both the endoscope 2 and the video processor 3.

In the electric power consumption reducing processing in the first and second embodiments, when a predetermined condition is satisfied, the illumination light amount change processing may be executed in priority among the illumination light amount change processing and the compression amount change processing to prevent resolution decrease. Specifically, only the illumination light amount change processing may be executed. Alternatively, the illumination light amount change processing and the compression amount change processing may be executed so that an amount of reduction of electric power consumption of the battery 25A through the illumination light amount change processing is larger than an amount of reduction of electric power consumption of the battery 25A through the compression amount change processing. The predetermined condition may be, for example, a condition that the remaining amount of the battery 25A is smaller than the battery threshold value but close to the battery threshold value, or a condition that the temperature of the grasping portion 2Ba is higher than the temperature threshold value but close to the temperature threshold value and it is unlikely that the endoscope 2 anomalously stops or the user cannot grip the grasping portion 2Ba.

The electric power consumption reducing processing may include warning processing that warns the user about execution of the electric power consumption reducing processing in addition to the illumination light amount change processing, the compression amount change processing, and the brightness correction processing. The warning processing may be, for example, processing that causes the display unit 4 to display characters or the like indicating that the electric power consumption reducing processing is in execution.

What is claimed is:

1. A video processor comprising:
a processor configured to:
   generate an endoscope image by performing predetermined image processing on image data obtained by a wireless endoscope that is battery-driven;
   execute an electric power consumption reducing processing;
   determine whether one or more pieces of start information is acquired after insertion of the wireless endoscope, the one or more pieces of start information being at least one of information for starting video recording of the endoscope image or information for starting automatic diagnosis support processing using the endoscope image; and
   stop the electric power consumption reducing processing and execute a high image quality achieving processing in response to acquiring the one or more pieces of start information during execution of the electric power consumption reducing processing.

2. The video processor according to claim 1, wherein the predetermined image processing includes brightness correction processing that corrects brightness of the image data,
   wherein the electric power consumption reducing processing and the high image quality achieving processing each include illumination light amount change processing, and
   wherein the illumination light amount change processing changes an illumination light amount of an illumination element configured to illuminate an object and the brightness correction processing.

3. The video processor according to claim 1,
wherein, in executing the electric power consumption reducing processing, the processor is configured to decrease an illumination light amount relative to when the electric power consumption reducing processing is not executed, and decrease a brightness parameter of the endoscope image relative to when the electric power consumption reducing processing is not executed.

4. The video processor according to claim 1,
wherein the processor is further configured to:
  acquire information related to a temperature of a grasping portion of the wireless endoscope;
  determine whether the temperature of the grasping portion is equal to or higher than a predetermined temperature threshold value; and
  execute the electric power consumption reducing processing in response to determining that the temperature of the grasping portion is equal to or higher than the predetermined temperature threshold value.

5. An endoscope system comprising:
an endoscope comprising:
  an image pickup device configured to generate image data through image pickup of an object; and
  an illumination element configured to illuminate the object;
a video processor comprising a processor; and
a power source configured to supply electric power to the image pickup device and the illumination element,
wherein the processor is configured to:
  generate an endoscope image by performing predetermined image processing on the image data;
  execute an electric power consumption reducing processing;
  determine whether one or more pieces of start information is acquired after insertion of the endoscope, the one or more pieces of start information being at least one of information for starting video recording of the endoscope image or information for starting automatic diagnosis support processing using the endoscope image;
  stop the electric power consumption reducing processing and execute a high image quality achieving processing in response to acquiring the one or more pieces of start information during execution of the electric power consumption reducing processing.

6. The endoscope system according to claim 5,
wherein the endoscope further comprises a grasping portion configured to be grasped by a user,
wherein the power source comprises a battery provided in the endoscope and configured to supply electric power to the image pickup device and the illumination element, and
wherein the processor is further configured to:
  acquire one or more pieces of environment information, the one or more pieces of environment information being at least one of information related to a temperature of the grasping portion of the endoscope or information related to a remaining amount of the battery; and
  determine whether to execute the electric power consumption reducing processing based on the one or more pieces of environment information.

7. The endoscope system according to claim 6,
wherein the processor is further configured to:
  determine at least one of whether the temperature of the grasping portion of the endoscope is equal to or higher than a predetermined temperature threshold, and whether the remaining amount of the battery is less than a predetermined battery remaining amount threshold; and
  execute the electric power consumption reducing processing in response to determining at least one of the temperature of the grasping portion of the endoscope is equal to or higher than the predetermined temperature threshold value and the remaining amount of the battery is less than the predetermined battery threshold.

8. The endoscope system according to claim 5,
wherein the electric power consumption reducing processing comprises at least illumination light amount change processing, compression amount change processing and brightness correction processing,
wherein the illumination light amount change processing changes an illumination light amount of the illumination element,
wherein the compression amount change processing changes a data amount of the compressed data, and
wherein the brightness correction processing corrects brightness of the image data, the brightness correction processing is processing in which a brightness parameter that defines a relation between brightness of the image data before correction and brightness of the image data after correction is used.

9. The endoscope system according to claim 5,
wherein, in executing the electric power consumption reducing processing, the processor is configured to:
  decrease an illumination light amount relative to when the electric power consumption reducing processing is not executed, and
  decrease a brightness parameter of the endoscope image relative to when the electric power consumption reducing processing is not executed.

10. The endoscope system according to claim 5,
wherein, in executing the high image quality achieving processing, the processor is configured to perform at least one of:
  increase an illumination light amount relative to when the high image quality achieving processing is not executed;
  increase a data amount of the compressed data relative to when the high image quality achieving processing is not executed; and
  decrease brightness of the endoscope image relative to when the high image quality achieving processing is not executed.

11. The endoscope system according to claim 6,
wherein at least one of the endoscope and the processor is further configured to perform:
  acquire the information for starting video recording of the endoscope image; and
  acquire the information for starting automatic diagnosis support processing;
wherein the endoscope is configured to perform:
  acquire the information related to the temperature of the grasping portion of the endoscope; and
  acquire the information related to the remaining amount of the battery.

12. The endoscope system according to claim 5,
wherein the endoscope is configured to acquire the at least one of information for starting video recording of the endoscope image or the information for starting automatic diagnosis support processing using the endoscope image.

13. The endoscope system according to claim 5,
wherein the video processor is configured to acquire the at least one of information for starting video recording of the endoscope image or the information for starting automatic diagnosis support processing using the endoscope image.

14. An image processing method comprising:
generating an endoscope image from image data obtained by a wireless endoscope that is battery-driven;
executing an electric power consumption reducing processing;
determining whether acquiring one or more pieces of start information after insertion of the wireless endoscope, the one or more pieces of start information being at least one of information for starting video recording of the endoscope image or information for starting automatic diagnosis support processing using the endoscope image; and
stopping the electric power consumption reducing processing and executing a high image quality achieving processing in response to acquiring the one or more pieces of start information during execution of the electric power consumption reducing processing.

15. The image processing method according to claim 14, wherein executing the electric power consumption reducing processing comprises:
decreasing an illumination light amount relative to when the electric power consumption reducing processing is not executed; and
decreasing a brightness parameter of the endoscope image than when the electric power consumption reducing processing is not executed.

16. The image processing method according to claim 14, wherein executing the high image quality achieving processing comprises at least one of:
increasing an illumination light amount relative to when the high image quality achieving processing is not executed;
increasing a data amount of the compressed data relative to when the high image quality achieving processing is not executed; and
decreasing brightness of the endoscope image relative to when the high image quality achieving processing is not executed.

17. The image processing method according to claim 14, further comprising:
acquiring information related to a temperature of a grasping portion of the wireless endoscope;
determining whether at least one of the temperature of the grasping portion of the wireless endoscope is equal to or higher than a predetermined temperature threshold; and
execute the electric power consumption reducing processing in response to determining the at least one of the temperature of the grasping portion of the wireless endoscope is equal to or higher.

18. The video processor according to claim 2,
wherein the brightness correction processing is processing in which a brightness parameter that defines a relation between brightness of the image data before correction and brightness of the image data after correction is used.

19. The endoscope system according to claim 5,
wherein the endoscope further comprises:
an endoscope processor configured to perform compression processing that generates compressed data by compressing the image data; and
a first wireless communication circuit configured to wirelessly transmit the compressed data,
wherein the power source comprises a battery provided in the endoscope and configured to supply electric power to the image pickup device, the illumination element, the endoscope processor, and the first wireless communication circuit,
wherein the video processor further comprises a second wireless communication circuit configured to receive the transmitted compressed data, and
wherein the processor is configured to generate the image data by decompressing the compressed data and perform the predetermined image processing on the image data generated by decompressing the compressed data.

20. The endoscope system according to claim 5,
wherein, in executing the electric power consumption reducing processing, the processor is configured to:
decrease an illumination light amount relative to when the electric power consumption reducing processing is not executed, and
decrease a brightness parameter of the endoscope image relative to when the electric power consumption reducing processing is not executed, and
wherein, in executing the high image quality achieving processing, the processor is configured to perform at least one of:
increase an illumination light amount is larger than relative to when the high image quality achieving processing is not executed;
increase a data amount of the compressed data relative to when the high image quality achieving processing is not executed; and
decrease brightness of the endoscope image relative to when the high image quality achieving processing is not executed.

* * * * *